United States Patent
Griffiths et al.

(10) Patent No.: US 7,221,159 B2
(45) Date of Patent: May 22, 2007

(54) COMMUNICATION SYSTEMS FOR USE WITH MAGNETIC RESONANCE IMAGING SYSTEMS

(75) Inventors: David M. Griffiths, Pittsburgh, PA (US); George J. Misic, Allison Park, PA (US); William J. Monski, Sewickley, PA (US); Mo Shuen Ng, Pittsburgh, PA (US); John A. Brosovich, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 1226 days.

(21) Appl. No.: 10/064,846

(22) Filed: Aug. 22, 2002

(65) Prior Publication Data

US 2003/0058502 A1 Mar. 27, 2003

Related U.S. Application Data

(63) Continuation-in-part of application No. 09/586,140, filed on Jun. 2, 2000, now Pat. No. 6,704,592.

(51) Int. Cl.
*G01V 3/00* (2006.01)
(52) U.S. Cl. ...................... 324/318; 324/322
(58) Field of Classification Search ........... 324/318, 324/322, 219, 309, 307, 300; 600/410, 445
See application file for complete search history.

(56) References Cited

U.S. PATENT DOCUMENTS 3,523,523 A 8/1970 Reich et al.

(Continued)

FOREIGN PATENT DOCUMENTS

DE 44 40 619 8/1995

(Continued)

OTHER PUBLICATIONS

Nishiura, N., et al., "An Optical and RF Telemetry Drug Injection Control and ECG System For Awake Small Animal Studies," Proceedings of the Annual International Conference of the Engineering in Medicine and Biology Society, Orlando, FL, IEEE, vol. 13, Conf. 5, pp. 2162-2163 (1991).

(Continued)

*Primary Examiner*—Brij B. Shrivastav
(74) *Attorney, Agent, or Firm*—James Stevenson; Gregory Bradley

(57) ABSTRACT

An antenna coupling enables communication across a barrier to radio frequencies. The antenna coupling comprises first and second antennas. The first antenna is adapted for positioning on a first side of the barrier, and is capable of receiving from and transmitting to a first transceiver disposed on the first side. The second antenna is adapted for positioning on a second side of the barrier, and is capable of receiving from and transmitting to a second transceiver on the second side. The interconnection of the first and second antennas through the barrier comprises the antenna coupling. The antenna coupling enables the first and second transceivers to communicate across the barrier over the desired range(s) of radio frequencies. In a related aspect, the antenna coupling may also include a filter interconnected between the first and second antennas to prevent radio frequencies outside of the desired range(s) from being transmitted across the barrier.

48 Claims, 11 Drawing Sheets

U.S. PATENT DOCUMENTS

| | | | |
|---|---|---|---|
| 3,812,843 A | 5/1974 | Wootten et al. | |
| 3,880,138 A | 4/1975 | Wootten et al. | |
| 3,888,239 A | 6/1975 | Rubinstein | |
| 4,006,736 A | 2/1977 | Kranys et al. | |
| 4,044,757 A | 8/1977 | McWhorter et al. | |
| 4,502,488 A | 3/1985 | Degironimo et al. | |
| 4,585,009 A | 4/1986 | Barker et al. | |
| 4,613,328 A | 9/1986 | Boyd | |
| 4,619,653 A | 10/1986 | Fischell | |
| 4,677,980 A | 7/1987 | Reilly et al. | |
| 4,695,271 A | 9/1987 | Goethel | |
| 4,737,712 A * | 4/1988 | Stormont et al. | 324/307 |
| 4,840,620 A | 6/1989 | Kobayashi et al. | |
| 4,854,324 A | 8/1989 | Hirschman et al. | |
| 4,885,538 A | 12/1989 | Hoenniger, III et al. | |
| 4,981,137 A | 1/1991 | Kondo et al. | |
| 5,027,824 A | 7/1991 | Dougherty et al. | |
| 5,030,201 A | 7/1991 | Palestrant | |
| 5,134,373 A | 7/1992 | Tsuruno et al. | |
| 5,236,417 A | 8/1993 | Wallis | |
| 5,244,461 A | 9/1993 | Derlien | |
| 5,269,762 A | 12/1993 | Armbruster et al. | |
| 5,274,330 A | 12/1993 | Rindlisbacher et al. | |
| 5,300,031 A | 4/1994 | Neer et al. | |
| 5,342,298 A | 8/1994 | Michaels et al. | |
| 5,352,979 A | 10/1994 | Conturo | |
| 5,354,273 A | 10/1994 | Hagen | |
| 5,357,959 A | 10/1994 | Fishman | |
| 5,411,485 A | 5/1995 | Tennican et al. | |
| 5,417,213 A | 5/1995 | Prince | |
| 5,458,122 A | 10/1995 | Hethuin | |
| 5,464,014 A * | 11/1995 | Sugahara | 600/411 |
| 5,472,403 A | 12/1995 | Cornacchia et al. | |
| 5,494,036 A | 2/1996 | Uber, III et al. | |
| 5,862,803 A | 1/1999 | Besson et al. | |
| 5,994,984 A | 11/1999 | Stancil et al. | |
| RE36,648 E | 4/2000 | Uber, III et al. | |
| RE37,602 E | 3/2002 | Uber, III et al. | |
| 6,704,592 B1 * | 3/2004 | Reynolds et al. | 600/411 |
| 2003/0050555 A1 * | 3/2003 | Critchlow et al. | 600/420 |

FOREIGN PATENT DOCUMENTS

| | | |
|---|---|---|
| DE | 196 21 393 | 12/1997 |
| EP | 0 105 550 | 4/1984 |
| EP | 0 495 287 | 7/1992 |
| EP | 0 518 100 | 12/1992 |
| EP | 0 655 220 | 5/1995 |
| JP | 61-155846 | 7/1986 |
| JP | 1-223943 | 9/1989 |
| JP | 1-165010 | 11/1989 |
| JP | 1-303139 | 12/1989 |
| JP | 5-84296 | 4/1993 |
| JP | 7-178169 | 7/1995 |
| JP | 2752909 | 2/1998 |
| WO | WO 99/27847 | 6/1999 |
| WO | WO 01/92907 | 12/2001 |

OTHER PUBLICATIONS

"Market Scan," Diagnostic Imaging, p. 61 (Sep. 1988).
Injectron MRT Brochure, Medtron MR-Injector, Technical Data, date unknown.
CT/MR Injector Brochure, Ulrich GmbH & Co. KG, (Nov. 1999).
Mildenberger, A., "MR Jet Basic Configuration DM 29000," Automation GmbH (Feb. 11, 1998).
Saini, S., et al., "In Vitro Evaluation of a Mechanical Injector for Infusion of Magnetic Resonance Contrast Media," Technical Report, Investigative Radiology, vol. 26, No. 8, pp. 748-751 (Aug. 1991).
Angioject 3 Brochure, CGR, Paris, France (1975).
Mallinckrodt, Optistar MR Contrast Delivery System Brochure, OR00200 (Feb. 2000).
International Search Report for Counterpart PCT Application PCT/US01/40826.
"Medrad Targets Market for MRI," Allison Hargraves, Pittsburgh Business Times, vol. 7, No. 18, p1(2) (Dec. 21, 1987).
"Detection of Acute Avascular Necrosis of the Femoral Head in Dogs: Dynamic Contrast-Enhanced MR Imaging vs. Spin-Echo and STIR Sequences," AJR: 159, pp. 1255-1261, Dec. 1992.
"An Infusion Pump That Works in MRI," Anesth. Analg. 1993: 77, p. 645, Letters to the Editor.
Mallinckrodt Optistar MR Digital Injection System, Operator's Manual, 801900-A (Nov. 1999).
Mallinckrodt Optistar MR Digital Injection System, Service and Parts Manual, 801902-A (Apr. 2000).
Medrad Spectris MR Injection System Service Manual, Catalog No. SSM200 1, 92901-T-129, Rev. A (1996).
Medrad Spectris MR Injector Operation Manual, SOM 200E, 92901-T-107, Rev. E (1996).
Invivo Research Inc., Millennia 3155 MVS Monitor Operations Manual, IRI PN#9545, Release 3, (Mar. 1998).
Invivo Research Inc., Omni-Trak 3150 MRI Patient Monitor Operations Manual, (Jan. 1998).
Injektron 82 MRT User Instructions, Version MR2, pp. 5, 30 and 31, (Mar. 10, 1999).

* cited by examiner

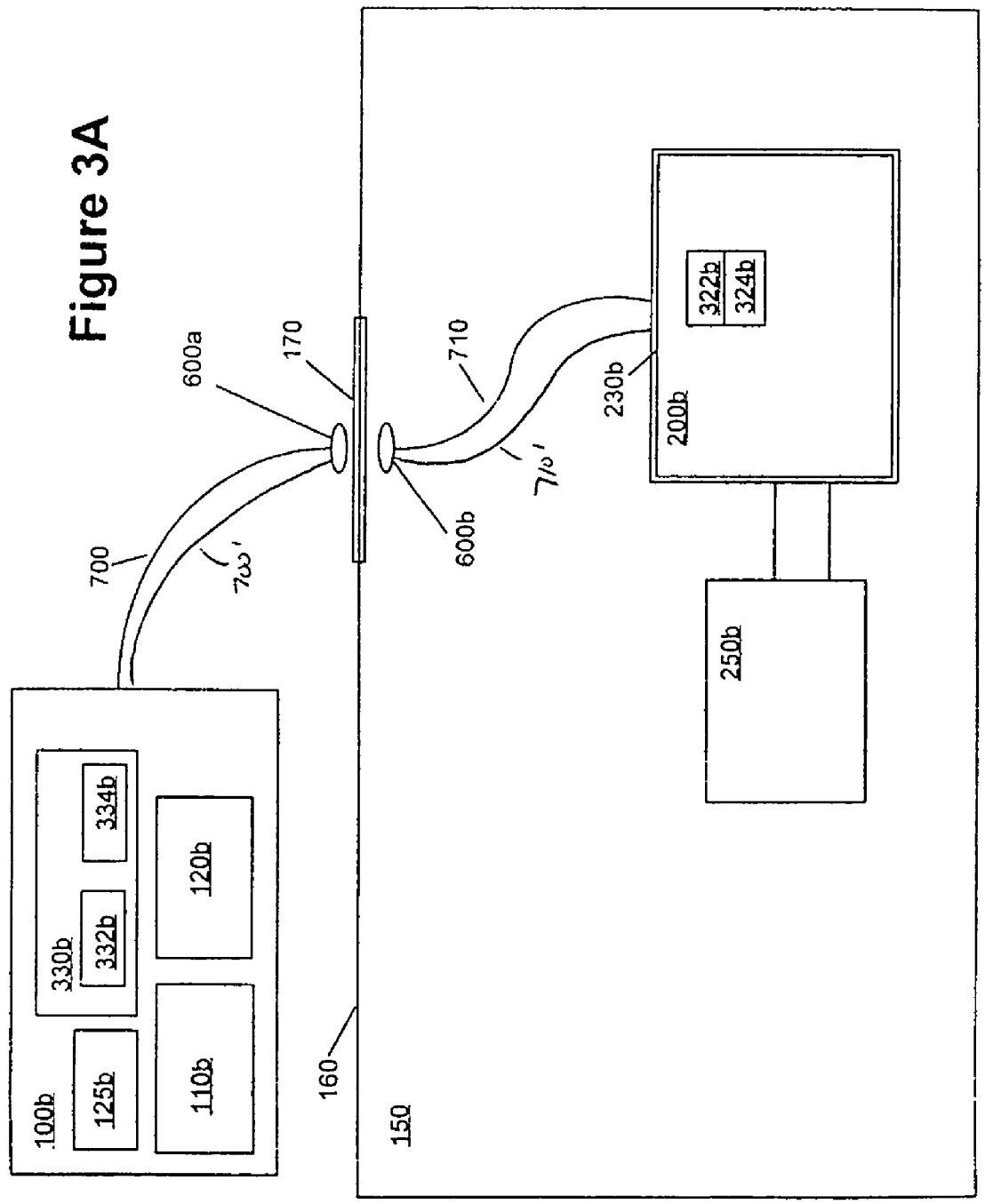

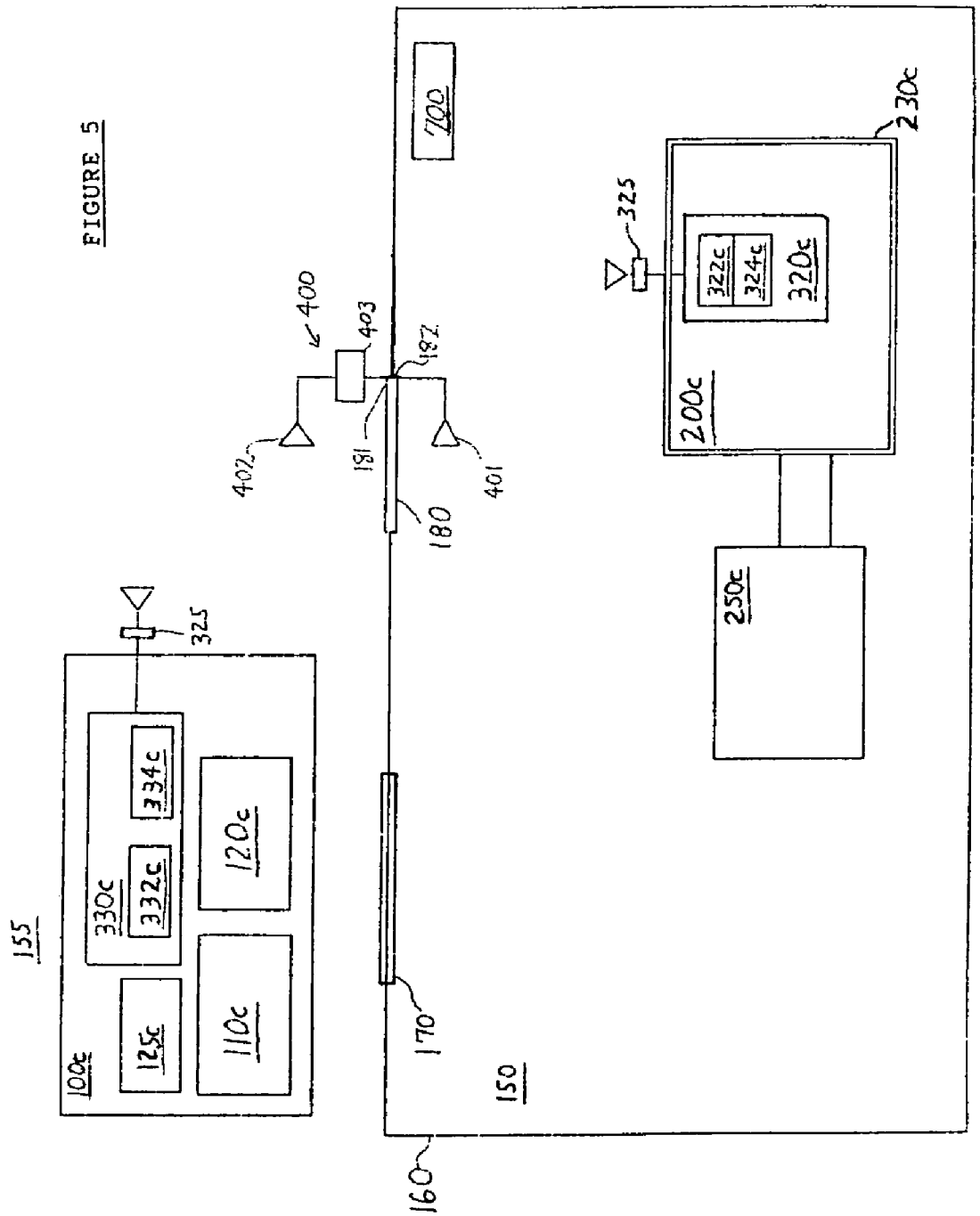

Figure 6A
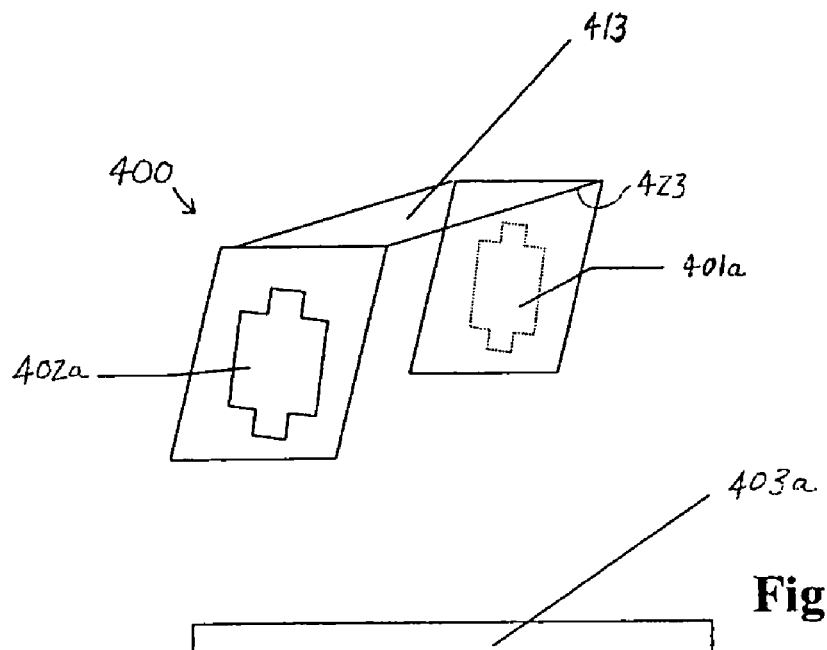
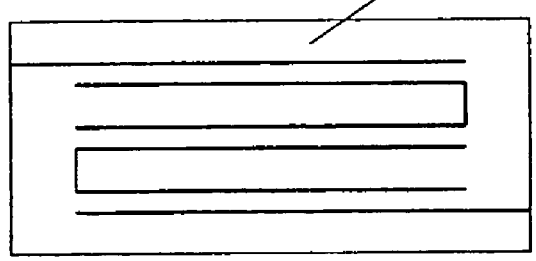
Microstrip filter
(Top view)
Figure 6B
Figure 6C
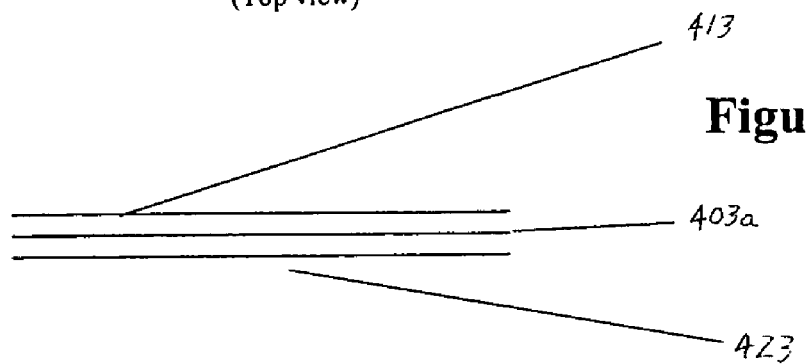

COMMUNICATION SYSTEMS FOR USE WITH MAGNETIC RESONANCE IMAGING SYSTEMS

CROSS REFERENCE TO RELATED APPLICATIONS

This application for patent is a continuation-in-part, and claims the benefit, of U.S. application Ser. No. 09/586,140, filed Jun. 2, 2000 now U.S. Pat. No. 6,704,592. The prior application has been assigned to the assignee of the invention(s) described and claimed below, and its teachings are incorporated into this document by reference.

FIELD OF THE INVENTION

The invention relates generally to systems and methods of communication, and, especially to systems and methods of communication for use in magnetic resonance imaging (MRI) and spectroscopy procedures. More particularly, the invention pertains to a system and method of wirelessly communicating between equipment located in, and which is movable within, the control and scanner rooms of an MRI suite.

BRIEF DESCRIPTION OF RELATED ART

The following information describes one of the many possible environments in which the invention can be used. It is provided to assist the reader to understand the invention, as novel material is often more readily understood if described in a familiar context. The terms used herein are not intended to be limited to any particular narrow interpretation unless expressly stated otherwise in this document.

In general, a magnetic resonance imaging (MRI) system requires isolation from external sources of radio frequency (RF) signals and electromagnetic fields to optimize the quality of the images obtainable during MRI scanning procedures. MRI systems therefore typically include some form of electromagnetic isolation shield or barrier. Most often, a room enclosed by copper sheeting or conductive mesh material isolates or shields the critical components (e.g., scanner, preamplifiers, receivers, local coils, etc.) of the MRI system from undesirable sources of electromagnetic radiation (e.g., radio signals, television signals, and other electromagnetic noise inherent in the atmosphere).

Several electrically powered injector systems have been developed for use in the MRI environment. These injectors systems are a potential source of electromagnetic radiation. Such injector systems are typically bifurcated, i.e., they have two pieces of equipment, namely, an injector control unit and a controller therefor. To realize the full benefit of "shielded" scanner rooms in MRI, the controller is typically isolated from the injector control unit that it controls. For example, the controller may be placed in the control room of the MRI suite, which is outside of the scanner room in which the scanner and the injector control unit operate. Such isolation prevents undesirable electromagnetic radiation generated by the controller of the injector system from interfering with the signals used to create the magnetic resonance images.

The remote location of the controller creates various problems associated with the installation and operation of these injector systems. One such problem is the need to provide a communication link between the externally located controller and the injector control unit within the shielded scanner room, without introducing extraneous electromagnetic radiation. In other words, there is a need to provide injector control circuitry while maintaining the integrity of the electromagnetic shield.

Previous attempts to solve these problems included drilling holes in the wall of the electromagnetically shielded room for inserting the necessary lines or, alternatively, laying the lines under the floor of the shielded scanner room. These alternatives have proven to be less than optimum because spurious electromagnetic radiation can arise, or be coupled into the scanner room from external sources, from the presence of the various supply cables within the shielded room of the MRI suite. Additionally, the MRI systems that employ these alternatives often require substantial site dedication and are, therefore, not very portable.

U.S. Pat. No. 5,494,036, the disclosure of which is incorporated herein by reference, discloses, in one embodiment, an improved communication link that is made through a window in a wall of the shielded scanner room. These windows are typically in the form of a glass laminate in which is sandwiched a conductive wire mesh. Alternatively, such a window may be coated with a thin sheet of conductive material, such as gold, to maintain the shielding characteristics of the scanner room.

The above-noted embodiment of the communications link of U.S. Pat. No. 5,494,036 includes electromagnetic transceivers that operate in a frequency range that permeates the window while maintaining the integrity of the shielded room. Specifically, the internal transceiver is positioned on the window and is tethered or otherwise attached via a communication line to the injector control unit located within the shielded scanner room of the MRI suite. The external transceiver is positioned on the opposite side of the window (i.e., in the control room of the MRI suite) and is connected to the controller of the injector system. Infrared or electromagnetic energy in the visual range was noted as providing the best results. Also disclosed is a fiber optic link through which the controller in the control room and the injector control unit in the shielded room can communicate without generating electromagnetic interference (EMI).

In general, U.S. Pat. No. 5,494,036 and related art disclose various ways of communicating between the control room and the scanner room through the electromagnetic isolation barrier separating them. Such communication is typically accomplished through the window using transceivers designed to operate in the infrared or visual ranges of the electromagnetic spectrum. It can also be done using a radio frequency (RF) shielded cable routed through a "tuned port" in the wall of the shielded room. The RF cable must be shielded, grounded and filtered to ensure that no external RF signals or other noise is coupled into the scanner room and thus defeat the purpose of the electromagnetic shield. The tuned port is a small, specially configured opening designed to prevent transmission of frequencies therethrough that could adversely affect the operation of the MRI system. It makes it possible, however, for the controller and injector control unit on the opposite sides of the shielded wall to communicate via the cable at frequencies particularly suited for transmission through such isolation barriers without substantial loss of signal or interference with the MRI scanner.

Although U.S. Pat. No. 5,494,036 and related art constitute an advance over earlier communications systems targeted for the MRI environment, there is still a need to develop communication systems that overcome the shortcomings inherent to such prior art. One such shortcoming is that the use of cables to connect to the transceivers on either side of the window inevitably restricts the mobility of both the controller and the injection control unit in the control and scanner rooms, respectively. The shortcomings of various other MRI communication systems are discussed in context below.

OBJECTIVES OF THE INVENTION

It is, therefore, an objective of the invention to provide a system and method of reliably communicating between the injection control unit located in the scanner room of an MRI suite and the controller therefor in the control room of the MRI suite.

Another objective of the invention is to provide a system and method of communicating reliably between the equipment located in the control and scanner rooms in which the equipment in either or both of the rooms can be moved without adversely affecting the quality of the communications or the images obtained during MRI scanning procedures.

Yet another objective is to provide a system and method of communicating wirelessly between the equipment located in the control and scanner rooms.

Still another objective is to provide a communications system and method capable of delivering reliable communications between the equipment located in the control and scanner rooms regardless of the field strength rating of the MRI system.

A further objective of the invention is to provide a communication system that is capable not only of providing wireless communication between the separated transceivers of one or more bifurcated equipment systems but also of enabling the full mobility of each piece of equipment within its respective area without adversely affecting the quality of the communications.

In addition to the objectives and advantages listed above, various other objectives and advantages of the invention will become more readily apparent to persons skilled in the relevant art from a reading of the detailed description section of this document. The other objectives and advantages will become particularly apparent when the detailed description is considered along with the drawings and claims presented below.

SUMMARY OF INVENTION

The foregoing objectives and advantages are attained by the various embodiments of the invention summarized below.

In a presently preferred embodiment, the invention provides a system of communicating for an injection system for use within a magnetic resonance imaging (MRI) suite. The MRI suite has a scanner room, a control room, and a barrier separating the two rooms. The system comprises a first transceiver, a second transceiver, a first antenna, and a second antenna. The first transceiver is situated within the scanner room in an injection control unit of the injection system. The second transceiver is situated within the control room in a controller of the injection system. The first antenna is positioned within the scanner room approximate an interior side of the barrier, and is capable of receiving from and transmitting to the first transceiver. The second antenna is positioned within the control room approximate an exterior side of the barrier, and is capable of receiving from and transmitting to the second transceiver. The first and second antennas are interconnected through the barrier to form an antenna coupling. The antenna coupling thus enables the controller and injection control unit to communicate therethrough across the barrier using a desired range of radio frequencies outside a range of, and without adversely affecting, the operation of the MRI suite.

In a broader application of the preferred embodiment, the invention provides a system of communicating for use within a magnetic resonance imaging (MRI) suite. The MRI suite has a scanner room, a control room, and a barrier separating them. The system features a first transceiver, a second transceiver, a first antenna, and a second antenna. The first transceiver is situated within the scanner room and is associated with a first piece of equipment. The second transceiver is situated within the control room and is associated with a second piece of equipment. The first antenna is positioned within the scanner room approximate an interior side of the barrier, and is capable of receiving from and transmitting to the first transceiver. The second antenna is positioned within the control room approximate an exterior side of the barrier, and is capable of receiving from and transmitting to the second transceiver. The first and second antennas are interconnected through the barrier to form an antenna coupling. The antenna coupling thus enables the first and second pieces of equipment to communicate therethrough across the barrier using a desired range of radio frequencies outside a range of, and without adversely affecting, the operation of the MRI suite.

According to the preferred embodiment, the invention also provides an antenna coupling for communicating across a barrier to radio frequencies. The antenna coupling comprises a first antenna and a second antenna. The first antenna is adapted to be positioned on a first side of the barrier, and is capable of receiving from and transmitting to a first transceiver disposed on the first side of the barrier. The second antenna is adapted to be positioned on a second side of the barrier, and is capable of receiving from and transmitting to a second transceiver disposed on the second side of the barrier. The interconnection of the first and second antennas through the barrier comprises the antenna coupling. The antenna coupling thereby enables the first and second transceivers to communicate therethrough across the barrier over the desired range(s) of radio frequencies. In a related aspect, the antenna coupling may also include a filter interconnected between the first and second antennas to prevent radio frequencies outside of the desired range(s) from being transmitted across the barrier.

In a preferred manifestation, the antenna coupling has its filter in the form of a microstrip filter, which is insulated within its own protective layer and sandwiched between conductive layers. The first and second antennas each take the form of patch antennas. The first patch antenna is interconnected to one end of the microstrip filter, and is capable of being positioned on the first side of the barrier. The second patch antenna is interconnected to the other end of microstrip filter, and is thus capable of being positioned on the second side of the barrier. In a related aspect, one of the conductive layers of the antenna coupling is adapted to be grounded and affixed to at least one of a jamb and an edge of a door of the barrier, such that the first and second antennas are situated on the first and second sides of the barrier, respectively. In a another related aspect, the antenna coupling may be implemented in a bracket-shaped configuration with the first and second patch antennas connected at a predetermined angle at the opposite ends of the microstrip filter.

In a variation of the preferred embodiment, the invention provides a system for communicating across the isolation barrier separating the scanner and control rooms of an MRI suite. The MRI suite is capable of accommodating a plurality of bifurcated equipment systems. Each of the bifurcated systems has an interior portion for placement within the scanner room and an exterior portion for placement within the control room. The system comprises a first antenna and a second antenna that are interconnected through the isolation barrier to form an antenna coupling. The first antenna is positioned within the scanner room, and is capable of receiving from and transmitting to a plurality of interior transceivers situated within the scanner room. Each of the interior transceivers is associated with the interior portion of one of the bifurcated systems corresponding thereto. The second antenna is positioned within the control room, and is capable of receiving from and transmitting to a plurality of exterior transceivers situated within the control room. Each of the exterior transceivers is associated with the exterior portion of one of the bifurcated systems corresponding thereto. Each of the exterior transceivers and the interior transceiver, corresponding thereto form a transceiver pair for one of the bifurcated systems through which the interior and exterior portions thereof communicate through the antenna coupling across the barrier using a desired range of radio frequencies assigned thereto outside a range of, and without adversely affecting, the operation of the MRI suite.

In a further variation, the invention provides an antenna coupling for communicating across a barrier to radio frequencies. The antenna coupling comprises a plurality of interior antennas and a plurality of exterior antennas. Each of the interior antennas is adapted to be positioned on an interior side of the barrier, and is capable of receiving from and transmitting to at least one interior transceiver disposed on the interior side of the barrier. Each of the exterior antennas is adapted to be positioned on an exterior side of the barrier, and is capable of receiving from and transmitting to at least one exterior transceiver disposed on the exterior side of the barrier. Each interior transceiver and the exterior transceiver corresponding thereto form a transceiver pair. Each interior antenna and the exterior antenna corresponding thereto are interconnected through the barrier to form an antenna pair to enable the transceiver pair(s) corresponding thereto to communicate therethrough across the barrier over a desired range of radio frequencies.

The invention also provides a method of communicating across an isolation barrier separating the scanner and control rooms of an MRI suite. The method comprises the steps of: (a) positioning first and second transceivers within the scanner and control rooms, respectively; (b) interconnecting a first antenna and a second antenna; and (c) positioning the first and second antennas within the MRI suite. The first antenna is positioned within the scanner room approximate an interior side of the barrier, and is capable of receiving from and transmitting to the first transceiver. The second antenna is positioned within the control room approximate an exterior side of the barrier, and is capable of receiving from and transmitting to the second transceiver. The method also includes the step of configuring the first and second transceivers to use a desired range of radio frequencies outside the range of operation of the MRI suite in communicating across the isolation barrier via the first and second antennas, and thus avoiding adverse affects upon the operation of the scanner in the MRI suite. In a related aspect, the method may also include the step of connecting a filter between the first and second antennas, preferably on the exterior side of the barrier, to prevent radio frequencies outside of the desired range from being transmitted across the isolation barrier.

It should be understood that the present invention is not limited to the general embodiments or the presently preferred embodiments and examples discussed above.

BRIEF DESCRIPTION OF DRAWINGS

The invention and its presently preferred embodiments will be better understood by reference to the detailed disclosure below and to the accompanying drawings, wherein:

FIG. 3A schematically illustrates a fourth embodiment of a communication system for the injection system shown in FIG. 1A, including passive optical communication of signals through the viewing window of the MRI suite between the injection control unit in the scanner room and the controller in the control room;

FIG. 5 illustrates the presently preferred embodiment of FIG. 4 in the context of an injection system in which the controller in the control room and the injection control unit in the scanner room communicate wirelessly via an antenna coupling;

FIGS. 6A, 6B and 6C illustrate a preferred manifestation of the antenna coupling of FIGS. 4 and 5, specifically one that could be fixed to a door between the control and scanner rooms so that one antenna thereof is positioned within the scanner room on the interior side of the shielded barrier and the other antenna thereof is positioned within the control room on the exterior side of the shielded barrier.

DETAILED DESCRIPTION

Figure 1A:
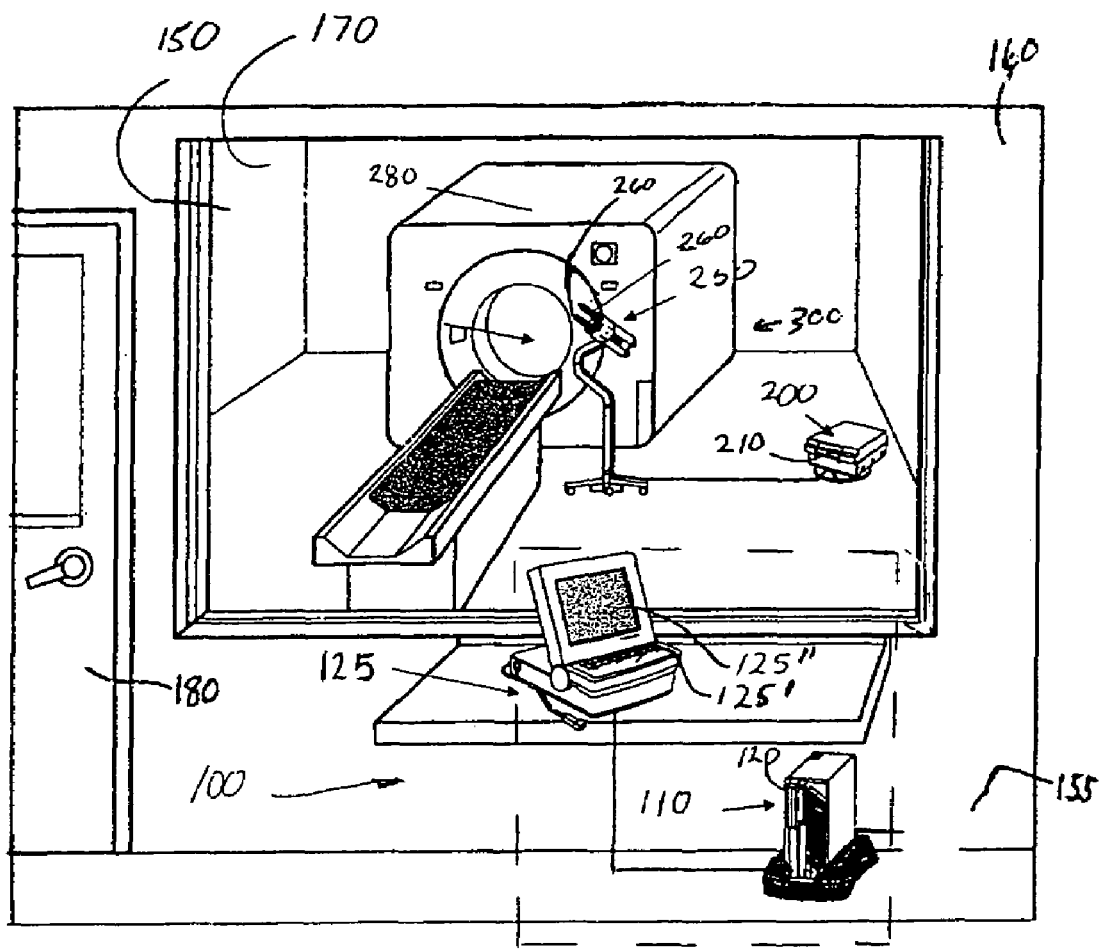
FIG. 1A is a generalized view of an MRI suite in which an injection control unit is located in the scanner room and the controller therefor is located in the control room.

FIG. 1A illustrates a magnetic resonance imaging (MRI) suite showing the scanner room 150 in the background, the control room 155 in the foreground, and the electromagnetic shield 160 that completely surrounds the scanner room and the MRI scanner 300 located within it. The electromagnetic shield 160 is typically composed of a copper sheet material or some other suitable conductive layer such as wire mesh. In a wall of the electromagnetic shield 160, the MRI suite also includes a door 180 and, preferably, a viewing window 170. The window 170 allows an observer and/or operator to see within the scanner room 150 without breaching the electromagnetic shield 160. Window 170 can be formed, for example, by sandwiching a wire mesh material (not shown) between sheets of glass or by coating the window with a thin coating of conductive material, such as gold (not shown), to maintain the continuity of the electromagnetic shield 160. The conductive layer also extends to the door 180, which when open allows access to the scanner room 150 and yet when closed is grounded to and constitutes a part of the electromagnetic shield 160. The shield 160 constitutes an isolation barrier that attenuates RF signals. The roof, floors, walls and door 180 of shield 160 provide approximately 100 decibels (dB) of attenuation, and the window 170 approximately 80 dB. Consequently, communication through shield 160 is difficult without some means of conducting signals through this isolation barrier.

An injection system is also shown in FIG. 1A. The injection system, for example, may be used to inject contrast media into the blood vessel of a patient undergoing an MRI procedure. As is well known in the MRI field, the contrast media serves to increase the contrast between the different types of tissues in the region of the body undergoing the scan, and thereby enhance the resolution of the images obtained during the scanning procedure. The illustrated injection system includes a controller 100 in control room 155 and the injection control unit 200 that it controls in scanner room 150. The controller 100 features a processing unit 110 (e.g., a digital microcomputer), a battery charger 120, and an operator interface 125. The interface 125 may include, for example, a data entry unit 125" and a display 125"'. As mentioned in background, the controller 100 is situated outside of the scanner room 150 and thus away from scanner 300, which is shielded from electromagnetic interference by shield 160.

The injection control unit 200 is preferably powered by a rechargeable battery 210. It also preferably includes control circuitry which controls electric motors 220 and 220", which are preferably located within injection control unit 200, as variously shown in FIGS. 1B, 1D, 2, and 3A. The injection control unit 200 itself is preferably contained within an electromagnetic shield 230 to reduce or eliminate any undesired electromagnetic radiation generated by electric motors 220 and 220" from interfering with the time varying magnetic fields generated by the scanner to produce the images.

Separation of the electric motors from the injection head 250, as well as the additional electromagnetic shielding, results in improved performance of the injection system and in improved quality of the images. Injection control unit 200 can be separated (for example, by ten to fifteen feet) from injection head unit 250, which is typically placed near the patient. Although the injection control unit 200 is preferably shielded to prevent RF interference, ferromagnetic material in injection control unit 200 can result in injection control unit 200 being drawn into magnet gantry 280. This undesirable consequence can result in damage to magnetic gantry 280, damage to injection control unit 200 and/or injury to personnel present in the scanner room 150.

Figure 1B:
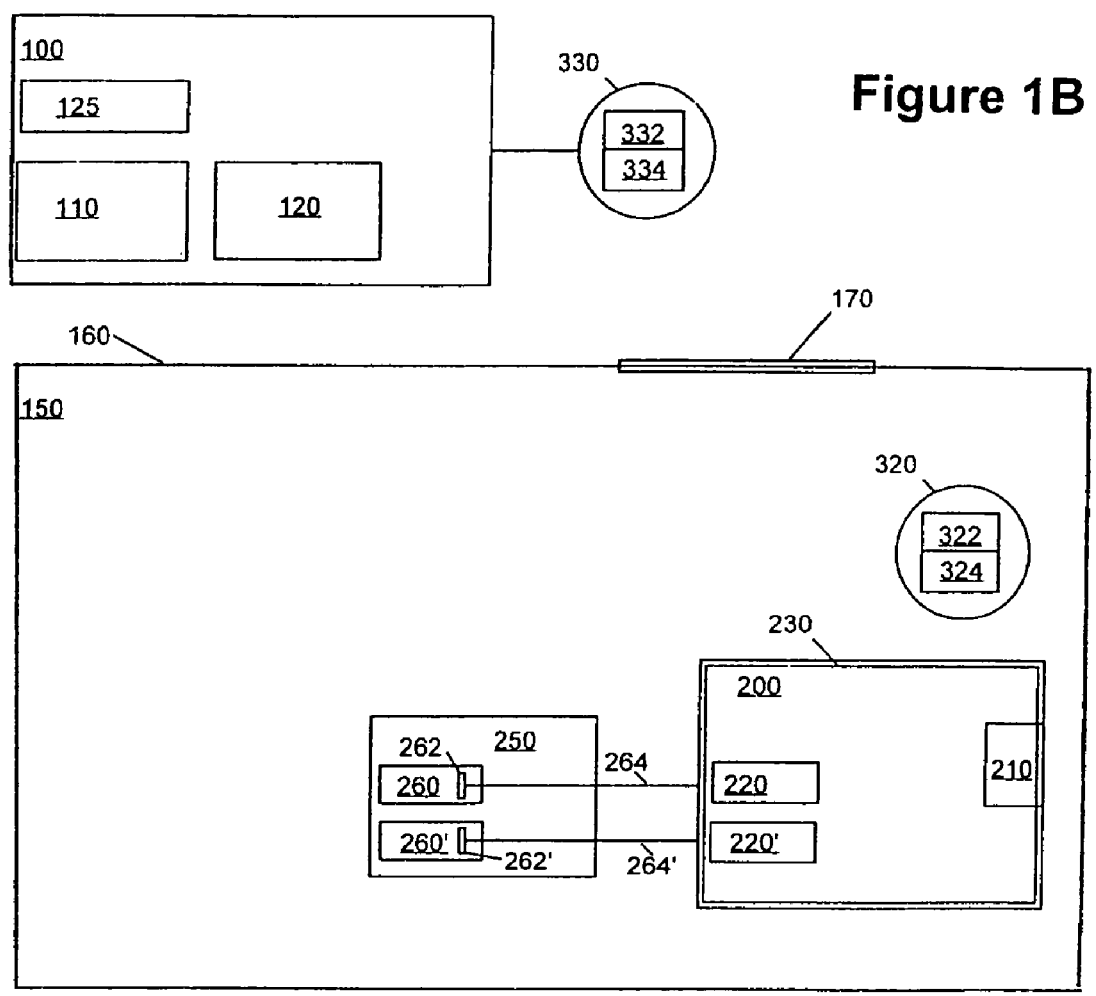
FIG. 1B schematically illustrates a first embodiment of a communication system for the injection system shown in FIG. 1A inclusive of the two communication units, one for the injection control unit and the other for the controller, on opposite sides of the window in the wall separating the scanner and control rooms of the MRI suite.

As best shown in FIG. 1B, injection head unit 250 further includes drive members (e.g., pistons) 262 and 262" that act to pressurize the contents of syringes 260 and 260", respectively, for injection into the patient. One or both syringes may contain contrast media or, alternatively, one may contain contrast media and the other a saline flush. Drive members 262 and 262" are preferably connected to electric motors 220 and 220", respectively, in injection control unit 200 by a non-rigid connection such as by flexible mechanical drive shafts 264 and 264", respectively. Drive shafts 264 and 264" are preferably made from a nonferrous metal such as hard brass. The injection head unit 250 is preferably located in close proximity to the patient to decrease the distance that the contrast media fluid must travel from the syringes 260 and 260".

Figure 1C:
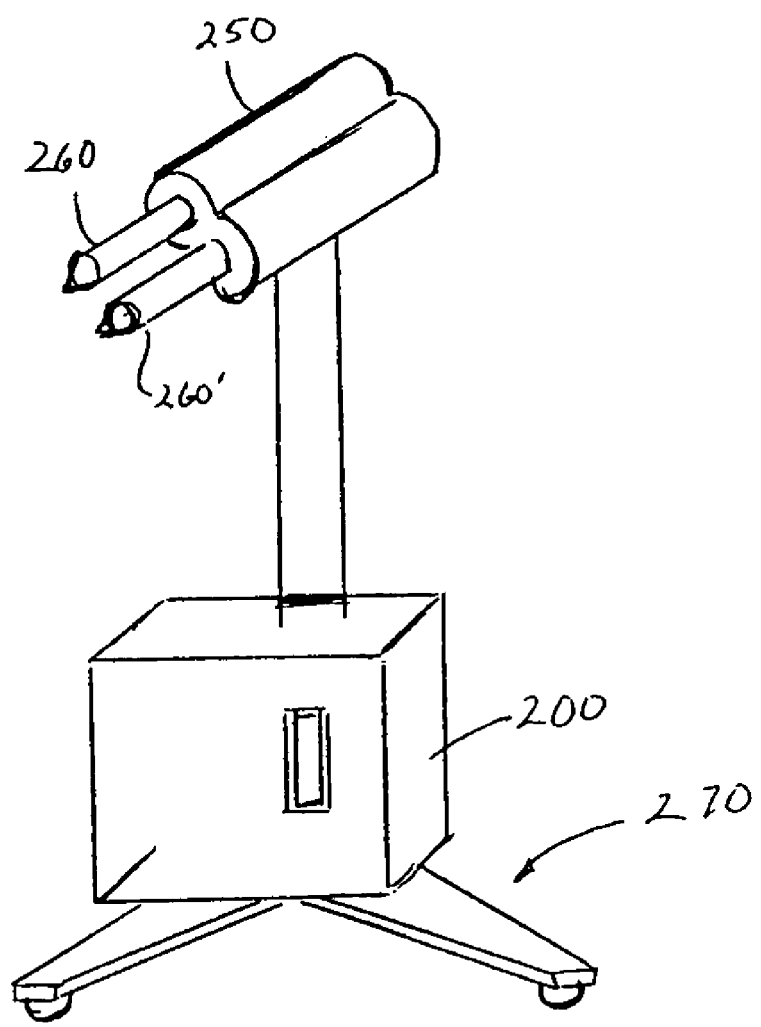
FIG. 1C illustrates an injector head and the mobile base unit on which it is mounted and to which the injection control unit is attached.

Injection control unit 200 can also be part of, or mounted onto, the same mobile base unit 270 as injection head unit 250, as illustrated in FIG. 1C. Particular care is taken to limit the amount of ferromagnetic material used in injection control unit 200. This prevents mobile base 270 from being drawn into magnet gantry 280 by the force of magnetic attraction generated by the main magnet of MRI scanner 300.

FIG. 1B illustrates a first embodiment of the present invention. For control of injection head unit 250 by system controller 100, communication must be maintained between the system controller 100 and the injection control unit 200. In this embodiment, the injector control unit 200 of the injection system is preferably in communication with a communication unit 320 that preferably includes a transmitter 322 and a receiver 324. Likewise, the controller 100 of the injection system is preferably in communication with a communication unit 330. Communication unit 330 preferably includes a transmitter 332 and a receiver 334. Transmitters and receivers for use in the present invention can also be combined in transceivers as is known in the art.

In one aspect of the present invention, transmitter 322 and receiver 324 of communication unit 320 are in wireless or cableless communication with those in communication unit 330. For example, there is preferably no communication line (e.g., fiber optic cabling or shielded electrical cabling) connecting injector control unit 250 to a generally stationary communication device positioned at window 170.

Wireless communication at any point between the injection control unit 200 in shielded room 150 and the controller 100 within control room 100 can increase the mobility of injection control unit 200, injection head unit 250 and/or personnel within room 150 by decreasing the amount of wiring in room 150. Communication unit 320 can, for example, be transportable/movable with the mobile base 270 shown in FIG. 1C. Injector head unit 250 and injector control unit 200 can thus be "untethered" and moved relatively freely to different positions within the shielded room 150. This increased mobility facilitates use thereof by, for example, facilitating positioning of injector head unit 250. Moreover, eliminating communication lines on the floor of scanner room 150 will significantly reduce, if not eliminate, the likelihood of tripping accidents.

Ideally, digital radio frequency (RF) energy that is outside the frequency range of the MRI scanner 300 will be used to transmit information to and/or from injector control unit 200. The imaging frequency of a 0.2 Tesla to 1.5 Tesla MRI scanner is typically in the range of approximately 8 Megahertz (MHz) to 64 MHz. A two-Tesla system may operate at an imaging frequency of up to approximately 85 MHz.

Furthermore, 3.0 Tesla MRI systems, which will eventually supersede many MRI systems having lower magnetic field strengths, will operate at frequencies up to approximately 128 MHz.

The communication system of the present invention will, therefore, preferably transmit and/or receive RF signals that are above approximately, say, 85 MHz for a 1.5 T MRI system or 140 MHz for a 3T MRI scanner. The allowable frequency range could even be below 8 MHz. More preferably, the RF signals will be above approximately 400 MHz. Most preferably, the RF signals will even be above 1 GHz (Gigahertz) as discussed further below. In that regard, RF signals outside of the imaging or operating frequency of the MRI scanner 300 can be transmitted through "leaks" or intentional RF gaps that act as leaks (for example, tuned ports or ventilation ports) in shield 160 without creating substantial interference with the imaging procedure. The ability of current isolation barriers, such as shield 160, to block RF signals is typically substantially reduced at frequencies above approximately 1 GHz, making RF signals above that frequency particularly suited for transmission through such barriers without substantial loss of signal or interference with scanner 300.

Figure 1D:
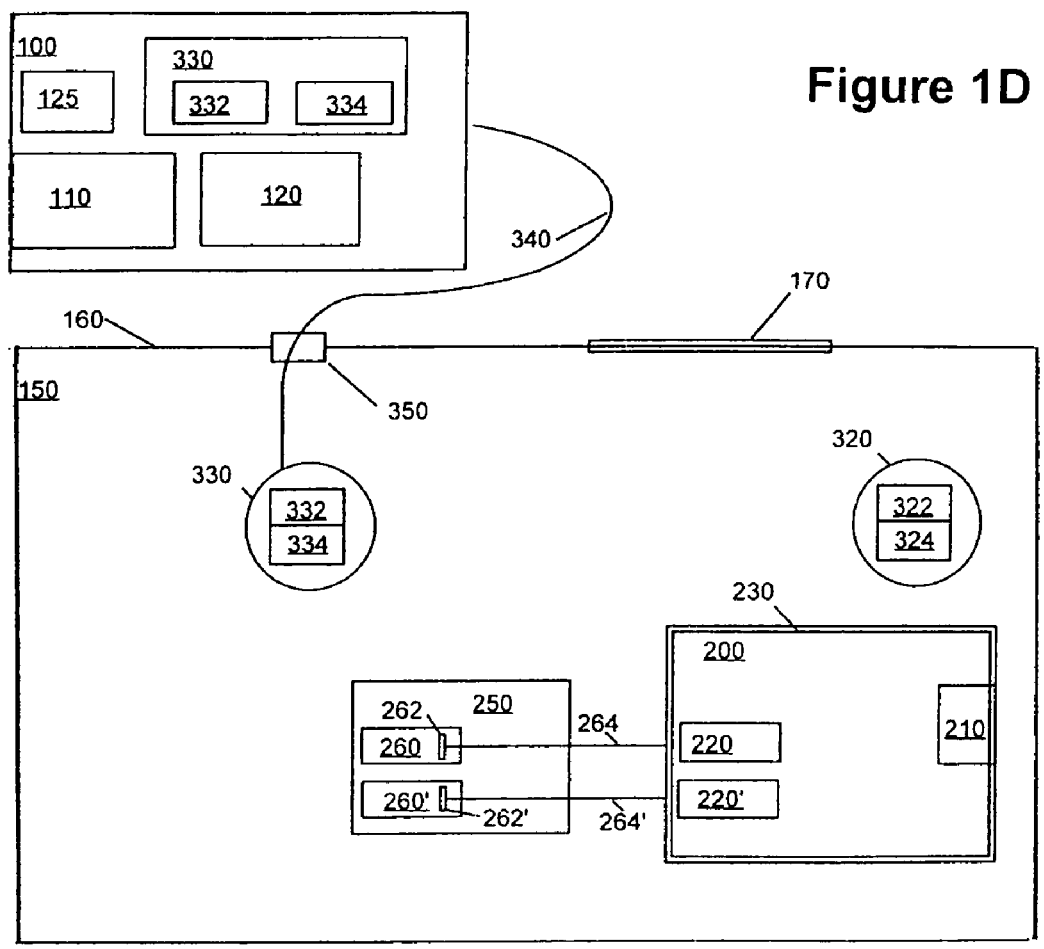
FIG. 1D schematically illustrates a second embodiment of a communication system for the injection system shown in FIG. 1A inclusive of two RF communication units, the first communication unit being situated within the scanner room and connected to the injection control unit and the second communication unit also within the scanner room yet connected to the controller in the control room by an RF cable routed through the tuned port in the wall separating the two rooms.

FIG. 1D illustrates a second embodiment of the present invention. In the embodiment illustrated in FIG. 1B, RF communication unit 330 (including, for example, transmitter 332 and receiver 334) is positioned outside of scanner room 150. In the embodiment of FIG. 1D, however, RF communication unit 330 is positioned within scanner room 150. Moreover, RF communication unit 330 is connected via a non-RF-interfering cabling 340 (for example, fiber optic cabling) through tuned port 350 to the controller 100 of the injection system, which is located in control room 155. As used herein and commonly in the MR arts, the term "tuned port" refers to an opening or aperture in shield 160 that is designed/dimensioned to prevent transmission of energy of certain frequencies therethrough. Communication unit 330 communicates with RF communication unit 320 as described above.

The RF energy used in the communications system of the present invention is preferably in the range of approximately 2.4 to 2.48 GHz, which is a band of energy set aside by the Federal Communication Commission (FCC) and other national organizations for industrial, scientific and medical (ISM) use. Operation in the 2.4 GHz ISM band allows license-free use and worldwide compliance. The 802.11b standard adopted by the Institute of Electrical and Electronic Engineering (IEEE) is a family of specifications created for wireless Ethernet local area networks. It provides a means of communicating wirelessly at very high speed without cumbersome wiring or significant expense. The IEEE 802.11b standard provides the technical guidance for developing wireless networks that use the 2.4 GHz radio band and run at 11 megabits per second (Mbps) using direct sequencing spread spectrum (DSSS) modulation. The IEEE 802.11a standard allows transmission at 5 GHz at up to 54 Mbps using Orthogonal Frequency Division Multiplexing (OFDM).

Because many other communications systems may use RF signals in the range of frequencies used in the present invention, it may be desirable to modulate the signal between controller 100 and injector control unit 200 to reduce or eliminate the potential for interference with or from such other communication systems. For example, DSSS modulation and frequency hopping spread spectrum (FHSS) modulation as known in the art may be used in the present invention. A detailed description of modulated transmissions is provided in WIT2410 2.4 GHz Spread Spectrum Wireless Industrial Transceiver Integration Guide (Jun. 15, 1999) available from Digital Wireless Corporation of Norcross, Ga., the disclosure of which is incorporated herein by reference. Spread spectrum modulation is currently used at 900 MHz and 2.4 GHz.

Even techniques such as FHSS modulation or DSSS modulation, however, are commonly used in RF communication devices, and the risk of interference with or from such other devices may still be unacceptably high. Therefore, one or more unique data authentication techniques can be used for RF communication in the present invention. For example, at least a part of a communication sequence signal may be transmitted at two or more different RF frequencies, all of which are outside of the frequency range of the MRI scanner 300. Data can be transmitted, for example, at 2.4 GHz and 5.8 GHz simultaneously. Transponder techniques may also be employed to deal with interference and to further improve the reliability of communication.

In general, any number of communication protocols or specifications can be used in digital RF transmission under the present invention. For example, the Bluetooth™ Technology of the Bluetooth Special Interest Group as set forth in the Bluetooth™ Specification Release 1.0, the disclosure of which is incorporated herein by reference, is suitable for use in the present invention. The Bluetooth™ specification specifies a system solution comprising hardware, software, and interoperability requirements. Radios that comply with the Bluetooth™ wireless specification operate in the unlicensed 2.4 GHz ISM radio spectrum. These radios can, for example, use a spread spectrum, frequency hopping, full-duplex signal at up to 1600 hops/sec. The signal hops among 79 frequencies at 1 MHz intervals to give a high degree of interference immunity. Up to seven simultaneous connections can established and maintained.

Furthermore, any type of energy that reduces or eliminates interference with the magnetic field used by the MRI scanner to generate an image is suitable in the present invention for transmitting information through the isolation barrier 160. For example, in addition to RF and other electromagnetic energy outside the frequency used by the MRI scanner, light energy (such as, visible light and/or infrared light), sonic energy, ultrasonic energy, and/or vibrational energy can be used.

Figure 2:
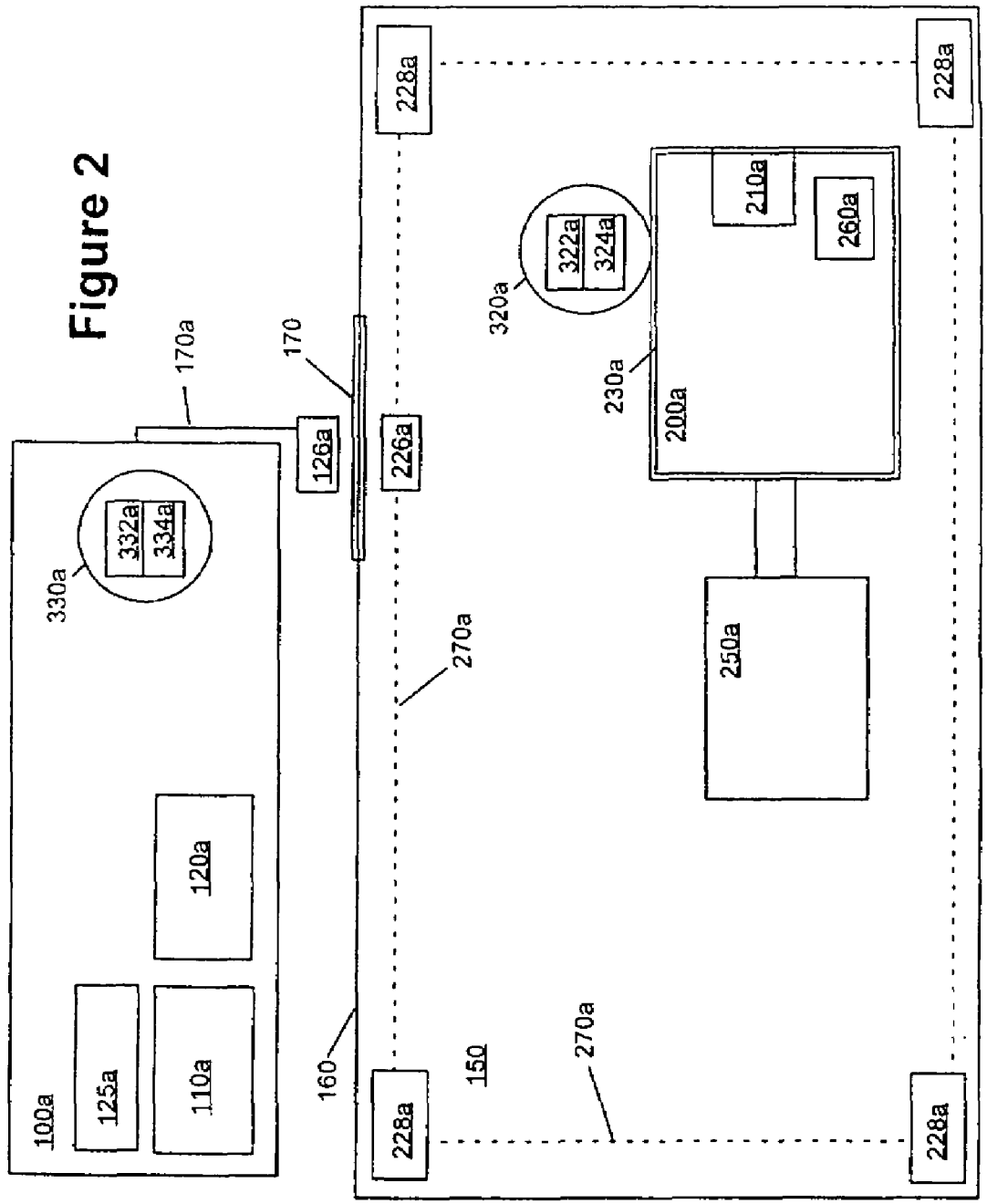
FIG. 2 schematically illustrates a third embodiment of a communication system for the injection system shown in FIG. 1A in which transceivers are placed on opposite sides of the window in the wall separating the scanner and control rooms.

FIG. 2 illustrates a third embodiment of the present invention. In this embodiment, the injector control unit 200a of the injection system includes a communication unit 320a. Communication unit 320a preferably includes a transmitter 322a and a receiver 324a. Likewise, the controller 100a of the injection system includes a communication unit 330a. Communication unit 330a features a transmitter 332a and a receiver 334a. As described above, the transmitter/receiver pairings can be in the form of transceivers.

In this embodiment, optical and/or infrared light is used to transmit information between controller 100a and injector control unit 200a through, for example, window 170. Such communication can be interrupted, however, if there is not a direct "line of sight" between the communication unit 330a of controller 100a and the communication unit 320a of injection control unit 200a. To assist in providing a substantially direct line of sight, an optical/infrared transceiver 126a in communication with communication unit 330a can, for example, be positioned at the outside of window 170 to transmit/receive optical/infrared signals through window 170. Signals to or from transceiver 126a can be transmitted directly from or to the communication unit 320a of injection control unit 200a. To further assist in providing a substantially direct line of communication, an optical/infrared transceiver 226a may also be positioned on the interior of window 170 to transmit to and receive signals from the communication unit 320a of injection control unit 200a. Furthermore, one or more intermediate/redirecting communication units 228a can be positioned at various locations about scanner room 150. Intermediate communication units 228a may, for example, be adapted to redirect/relay signals between, for example, transceiver 226a and communication unit 320a. In this manner, injector control unit 200a can be moved freely about scanner room 150 without losing communications with controller 100a.

Transceivers 126a and 226a and/or intermediate communication unit(s) 228a may also amplify or otherwise modify signals. For example, the signals between transceiver 126a and 226a may be in the form of light energy, ultrasonic energy, or vibrational energy. Transceiver 226a or intermediate communication unit(s) 228a may transform such signals into RF signals of an appropriate frequency (as described above) for communication with communication unit 320a of injection control unit 200a. Transceiver 226a and redirecting communication unit(s) 228a can be physically linked as represented by communication lines 270a in FIG. 2. Likewise, communication unit 330a and transceiver 126a can be connected by communication line(s) 170a. In this embodiment, like the embodiments of FIGS. 1B and 1D, communication unit 320a preferably remains untethered by any communication line.

Instead of RF energy, sonic and/or ultrasonic energy may, for example, be used to transmit information to and/or from communication unit 320a. Transceiver 226a and/or redirecting communications units 228a may, for example, transmit voice commands to communication unit 320a, which upon being relayed would be interpreted by a processing unit 260a in injection control unit 200a for control thereof.

In general, any type of energy that may be used to transmit information through the air to and/or from communication unit 320a and/or communication unit 330a and that does not substantially interfere with the MRI scanner (i.e., create unacceptable artifacts on an image) is suitable for use in the present invention.

Figure 3B:
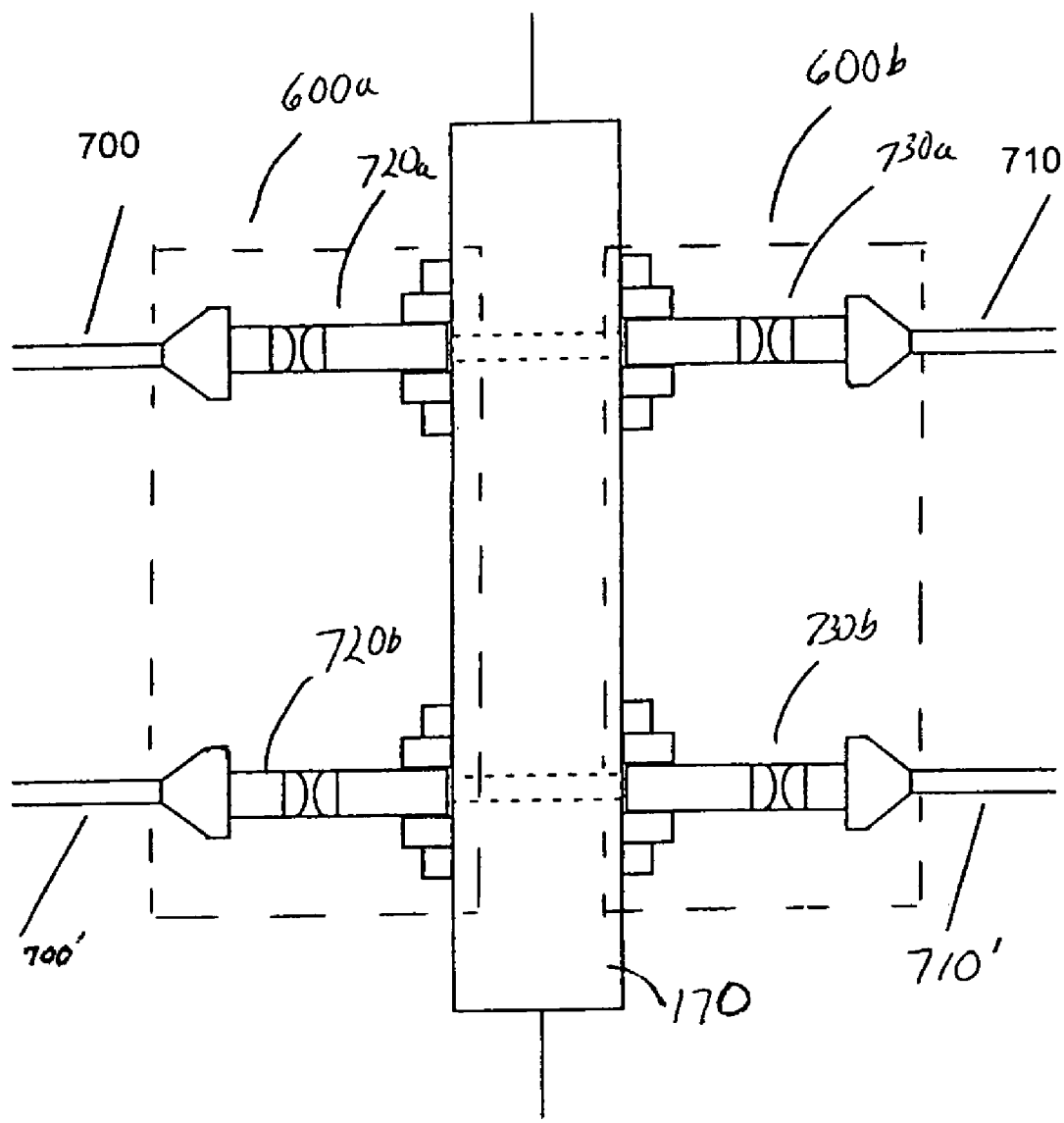
FIG. 3B illustrates an expanded view of the fourth embodiment shown in FIG. 3A in which light collimating devices 600a and 600b are employed.

FIGS. 3A and 3B illustrate a fourth embodiment of the present invention. In this embodiment, electromagnetic interference in an MRI procedure is reduced or eliminated through the use of a passive optic communicative coupling. In particular, the controller 100b in control room 155 is optically coupled with the injection control unit 200b in scanner room 150 for the purpose of controlling, among other functions, the operation of the injection head unit 250a. In that regard, the controller 100b includes a transmitter 332b and a receiver 334b. Transmitter 332b and receiver 334b are preferably connected to a light transmitting or collimating device 600a (e.g., one or more lenses) via fiber optic cabling 700 and/or 700". Light collimating device 600a is aligned with a second light transmitting or collimating device 600b on the interior of scanner room 150 through window 170. Light collimating device 600b is connected to a transmitter 322b and a receiver 324b positioned within injection control unit 200b via fiber optic cabling 710 and/or 710". By locating transmitter 322b and receiver 324b within shielded housing 230b of injection control unit 200b, electromagnetic interference therefrom can be greatly reduced or eliminated.

FIG. 3B illustrates an expanded view of the light collimating devices 600a and 600b used to optically communicate through window 170. In general, light collimating devices 600a and 600b preferably act to transmit/focus one or more columns or beams of light (e.g., visible light such as bright LCD light) for passage through window 170. As shown in FIG. 3B, collimating device 600a includes a first lens assembly 720a and a second lens assembly 720b. Lens assembly 720a is in communication with transmitter 332b via fiber optic cable 700, while lens assembly 720b is in communication with receiver 334b via fiber optic cable 700". Collimating device 600b includes a third lens assembly 730a and a fourth lens assembly 730b. Lens assembly 730a is in communication with receiver 324b via fiber optic cable 710, while lens assembly 730b is in communication with transmitter 322b via fiber optic cable 710". In one manifestation, convex lens having a 25 mm diameter and a focal length of 9 mm were used in all lens assemblies 720a, 720b, 730a and 730b. Lens assembly 720a is aligned with lens assembly 730a such that information in the form of a beam of light can be transmitted between transmitter 332b and receiver 324b. Likewise, lens assembly 720b is aligned with lens assembly 730b such that information in the form of a beam of light can be transmitted between transmitter 322b and receiver 334b. Bi-directional transmission of data can also be achieved using a single lens assembly on each side of window 170 by, for example, multiplexing the transmission of data.

Information can be transmitted via light energy using a protocol such as the Ethernet 10BaseT protocol. Examples of transceivers and receivers suitable for use in the present invention include the HFBR 1527 transmitter and the HFBR 2526 receiver available from the Hewlett Packard Company.

Data transmission rates of, for example, 10 Mbps and higher are possible in the embodiment of FIGS. 3A and 3B. Moreover, by positioning transmitter 322b and receiver 324b (or a transceiver) within shielded housing 230b of injection control unit 200b and passively transmitting light between collimating devices 600a and 600b, potentially interfering electromagnetic fields are reduced as compared, for example, to the system of U.S. Pat. No. 5,494,036 in which a transceiver is positioned at the viewing window and connected to the injection control unit thereof via shielded cabling.

The techniques disclosed above, however, have several limitations. First, not all MRI suites have a window in the wall separating the control and scanner room, although most do. Consequently, any given communication technique that relies on the presence of a window as an optical conduit would not be able to be applied to all MRI suites. Second, the shielding between the control and scanner rooms 155 and 150 may vary substantially among MRI suites. Thus, the varying optical and electromagnetic properties of the windows may adversely affect the performance of the communication system in any given MRI suite. Third, as scanner technology improves and MRI magnets move to greater strengths and scanner equipment becomes more sensitive, the shielding will inevitably improve. Such improvements, for example, may take the form of using double mesh screening in the windows, which will causing even greater optical and electromagnetic attenuation of the signals that would need to be communicated between the control and scanner rooms. This, of course, would impair, or perhaps even completely degrade, the operation of such transceiver based communication systems. Fourth, when using such transceivers, each transceiver must ultimately be connected to its associated piece of equipment on its side of the window, and this connection takes the form of fiber optic or electrical cables. Such connection schemes, however, restrict the mobility of the pieces of equipment in either or both of the control and scanner rooms. Lastly, the communications equipment (e.g., transceivers), whether near or on the window, may at least partially block the window, and thus obstruct the view of the operator from the control room into the scanner room.

In addition, there are some products, such as patient physiologic monitoring systems from Invivo Research Inc. (Orlando, Fla.) and injection systems from Medtron Medical Systems, Inc. (Saarbrücken, Germany), that use RF communication techniques in the MR environment that rely on leakage in the shielding 160 at high RF frequencies. There is anecdotal evidence, however, that these systems have unreliable communication, which may be a function of the orientation and placement of the equipment. For example, the antennas for these systems must sometimes be placed in front of the window 170, which may have reduced attenuation properties at high frequencies, to allow enough signal level for successful communication. If the antennas are moved, the communication between the separate pieces of equipment in the control and scanner rooms 155 and 150 may be intermittent.

FIGS. 4–7 illustrate a presently preferred embodiment of the invention, one that overcomes the limitations of the prior art and the previously disclosed embodiments. This embodiment of the communication system allows the controller 100c in control room 155 and the injection control unit 200c in scanner room 150 not only to communicate wirelessly through shield 160 but also to enable the separate pieces of equipment to which they are attached to be mobile within their respective rooms. As will become apparent from the description below, the essential inventive concepts of this communication system can be applied not only to injection systems but also to other systems applicable to the MRI environment. Examples of such other systems include patient monitors, infusion pumps, temperature probes, pressure monitors, ventilators, gating devices, stimulation devices for functional imaging, and audio and video systems. The concepts can be applied conceivably to any device or system that allows remote control and/or monitoring of diagnostic and therapeutic devices within the scanner room. The concepts could even be applied to devices and systems through which to remotely control and/or monitor the environment within the scanner room. Consequently, although this preferred embodiment is described below in the context of injection systems, the reader should understand that the invention may also be applied or adapted to other types of bifurcated equipment systems.

Figure 4:
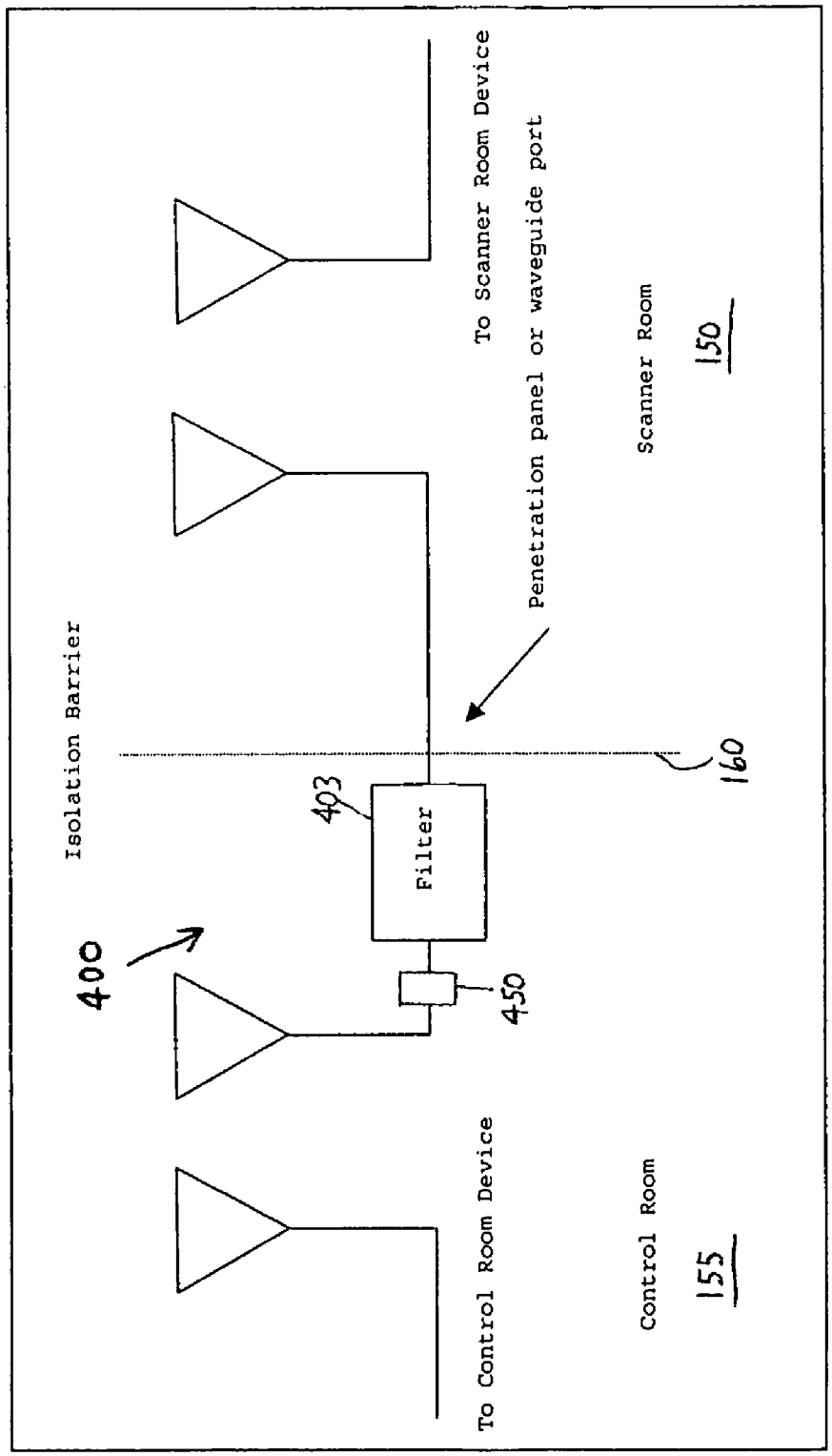
FIG. 4 illustrates a presently preferred embodiment of a communication system that is capable not only of providing wireless communication between the injection control unit in the scanner room and the controller in the control room but also of enabling the full mobility of such equipment within their respective rooms.

FIGS. 4 and 5 illustrate the preferred embodiment of the communication system in the context of an injection system in which the controller 100c in control room 155 and the injection control unit 200c in scanner room 150 communicate wirelessly via an antenna coupling 400. In this arrangement, the communication system comprises a first transceiver 320c with its associated antenna in scanner room 150 and a second transceiver 330c with its associated antenna in control room 155, in addition to the antenna coupling 400. In its most basic configuration, the antenna coupling 400 includes a first antenna 401 interconnected to a second antenna 402. The first antenna 401 shall be positioned within the scanner room, and the second antenna 402 in the control room. Antenna coupling 400 also preferably includes a filter 403, which is preferably positioned on the control room side of the isolation barrier 160. Filter 403 assures that communication will occur over the desired range(s) of frequencies outside the range of, and without adversely affecting, the operation of the MRI suite, particularly with the operation of scanner 300 (see FIG. 1) therein.

The antennas 401 and 402 of antenna coupling 400 preferably employ a circularly polarized design. Spiral and helical antennas are suitable for this purpose. While potentially losing a nominal 3 dB of gain for each antenna, such antennas allow for more flexibility in the orientation and placement of controller 100c and injection control unit 200c on which the first and second antennas 401 and 402 are respectively placed. Many spiral antenna designs are also naturally broadband and could be used to operate at more than one range of frequencies. Antennas with reduced polarization effects can be useful in making certain that the communications method of the invention does not suffer from positional sensitivity. Should it be likely that the separate pieces of the bifurcated injection system will not be moved, antenna coupling 400 can employ directive antennas. Such antennas with greater gain/directivity may be used to optimize not only signal-to-noise ratio (S/N) but also the strength of the signals communicated between controller 100c and injection control unit 200c. It is preferable to place such directive antennas for increased signal gain in control room 155, where multipath effects are less likely than in scanner room 150. Antennas having a parabolic design, horn design, or a Yagi design are suitable for this purpose.

The filter 403 is frequency selective, and is employed to ensure that RF energy near the sensitive operating frequency (Larmor frequency) of the main magnet of scanner 300 does not enter or exit scanner room 150. Such a filter may be required on one or both sides of barrier 160, or specifically at the point at which the barrier is breached. Whether highpass, bandpass, bandstop or some combination thereof, such a filter(s) can provide, for example, 80 to 100 dB of attenuation at the Larmor frequency. As is known in the field of MRI, such filtering of unwanted RF emanations also serves to prevent artifacts from being produced within the images generated by the MRI system.

As can be readily understood from FIG. 5 and the description of the previous embodiments, first transceiver 320c is associated with, and conveys communications to and from, injection control unit 200c. Similarly, second transceiver 330c is associated with, and conveys communications to and from, the controller 100c of the injection system. Along with antenna coupling 400, transceivers 320c and 330c thus provide the necessary communication link between the control and scanner rooms, or, more accurately, the controller 100c and injection control unit 200c of the injection system.

In addition to filter 403, the communication system of the present invention may also include a filter 325 on one or both transceivers 320c and 330c. Such a filter can be used to remove any spectral leakage and subharmonics generated by the transceiver(s). It would also remove other electromagnetic noise generated by the transceiver(s) such as that which is typically generated as the transceiver is being turned on and/or off.

Referring still to FIGS. 4 and 5, the first and second antennas 401 and 402 of antenna coupling 400 are interconnected through the isolation barrier 160 that separates the scanner and control rooms 150 and 155. As noted previously, the isolation barrier 160 extends to the door 180 of the scanner room as well as the window 170. Therefore, the antenna coupling 400 is preferably adapted to be fixable to the door 180 or other entry way in such a manner that assures that the first and second antennas 401 lie on opposite sides of the electromagnetic shield 160. More particularly, like all doors, the door 180 of scanner room 150 has top, bottom, right and left edges against which the jambs of the door opening essentially abut when the door is closed. As shown in FIG. 5, the antenna coupling 400 can therefore be affixed to a jamb 181 of door 180, for example, with the first and second antennas being situated on opposite sides of barrier 160. Alternatively, the antenna coupling 400 could be routed through the tuned port or other opening in the wall of scanner room 150, as long as the first and second antennas 401 and 402 are on opposite sides of isolation barrier 160. The penetration panel in barrier 160, for example, provides such an opening, and typically includes one or more filtered BNC connections through which equipment inside the scanner room can be connected to equipment outside. The antenna coupling 400 of the present invention could thus be adapted to work with spare or newly installed BNC connections.

FIG. 6A illustrates a preferred manifestation of the antenna coupling 400 of FIGS. 4 and 5. In this manifestation, the filter 403 preferably takes the form of a microstrip filter 403a on a circuit card as best depicted in the top view of FIG. 6B. The microstrip filter 403a is preferably insulated within its own protective layer and sandwiched between conductive layers 413 and 423, as is best shown in FIG. 6C. The first antenna 401 preferably takes the form of a patch antenna 401a on a circuit card, as does second antenna 402 in patch antenna 402a. Patch antennas 401a and 402a are preferably connected at a predetermined angle to the opposite ends of the circuit card of microstrip filter 403a. This particular construction shown in FIG. 6A, for example, will enable the outer conductive layer 413 to be easily grounded and affixed to the jamb 181 for door 180, or alternatively or additionally, the inner conductive layer 423 to be grounded and affixed to the corresponding edge 182 of door 180. (See FIG. 5) Because the outer and inner conductive layers 413 and 423 contact the similarly conductive material on the edge 182 and/or the corresponding jamb 181 of door 180, installation of antenna coupling 400 will not leave an opening within, or otherwise disrupt the continuity of, the electromagnetic shield 160 that protects the MRI scanner 300 from undesirable sources of electromagnetic radiation. The same effect will be had, of course, if antenna coupling 400 is attached to the bottom edge of door 180.

Furthermore, although antenna coupling 400 is shown in FIG. 6A as having a bracket-shaped or open-ended square-shaped construction, the exact configuration selected will, of course, depend on the entry way one chooses through the electromagnetic shield 160. Consequently, a variety of geometric constructions can be used, including, for example, rectangle-shaped, U-shaped, or even line or planar-shaped configurations.

In operation, the antenna coupling 400 of FIG. 6A is ideally suited for communication at microwave frequencies, such as the 2.4–2.48 GHz radio spectrum of the Bluetooth™ wireless specification noted above. The microstrip filter 403a, when implemented as a high pass filter, may be constructed as a microwave stripline filter, waveguide filter or surface acoustic wave (SAW) filter. The high frequency signals used for such communication, which are substantially above the Larmor frequency of scanner 300, are not likely to cause interference with or be affected by the MRI system. A high pass filter with a cutoff point above the Larmor frequency and sufficient stop band attenuation (80 to 100 dB) will allow the desired RF transmissions to pass through antenna coupling 400. It will also effectively reduce any lower frequency signals that could potentially interfere with an MRI scan and thus create image artifacts. It would also filter out any potential RF leakage from scanner 300 to the external environment.

In a related aspect, the antenna coupling 400 may include one or more RF amplifiers 450, as best shown in FIG. 4. Without the use of RF amplifiers, the antenna coupling 400 passively relays transmissions between the controller 100c and injection control unit 200c. With an RF amplifier 450 connected between the first and second antennas 401 and 402 on the control room side of shield 160, the signals being conveyed between transceivers 320c and 330c will be amplified before being rebroadcast. This is shown generally in FIG. 4. In a variant of this setup, an RF amplifier 450 may also be connected adjacent to each of the first and second antennas 401 and 402 on either side of shield 160. Consequently, the antenna coupling 400 of the present invention may employ either passive or active retransmission of the RF signals. A transponder at the antenna coupling and/or at transceivers 320c and/or 330c could also be employed to further improve the reliability of communication.

Figure 7:
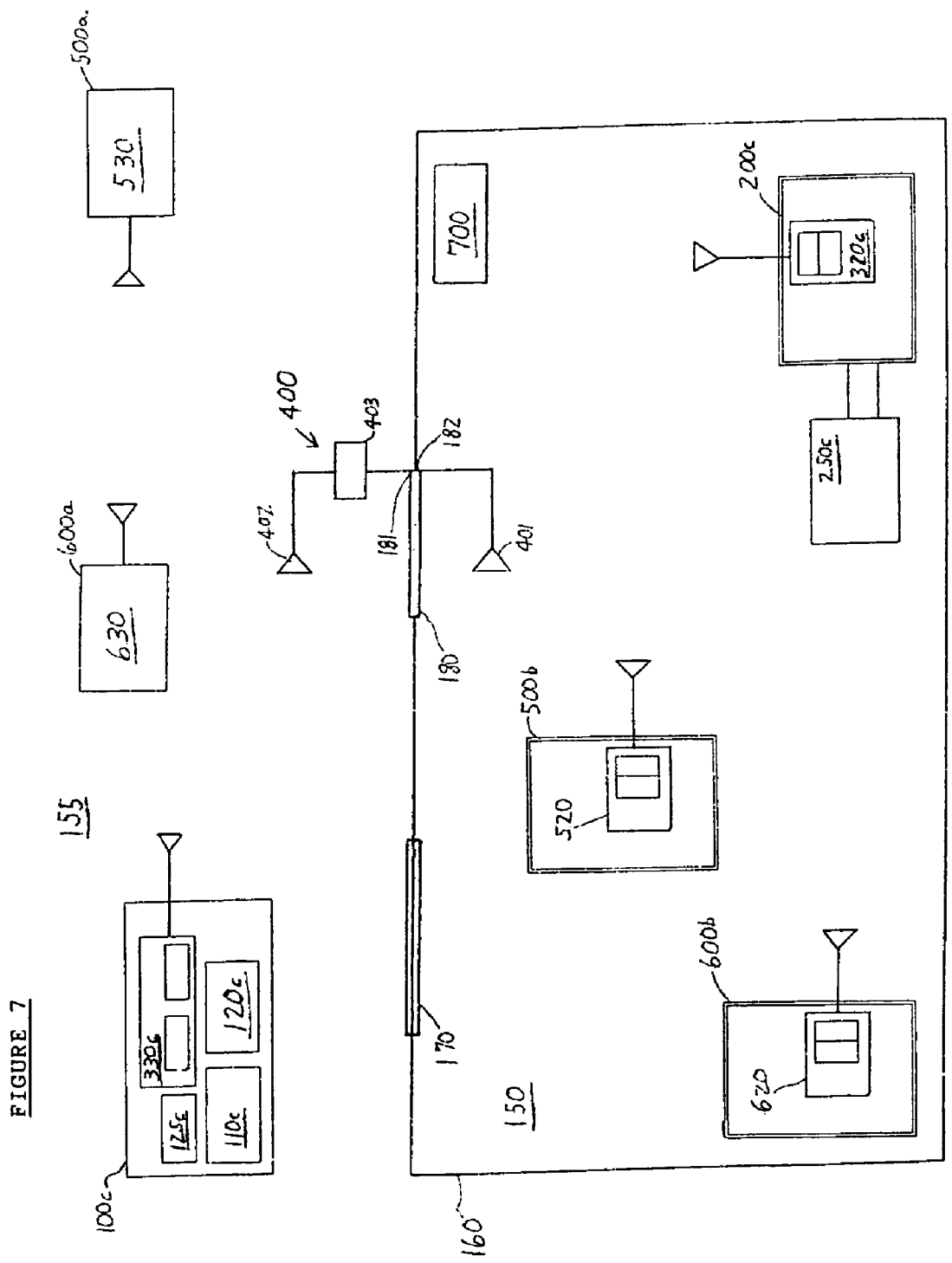
FIG. 7 illustrates the presently preferred embodiment of the communication system as it could be applied to provide wireless communication between the control and scanner rooms of the MRI suite for a plurality of bifurcated equipment systems.

FIG. 7 illustrates the presently preferred embodiment of the communication system as it could be applied to provide wireless communication between the control and scanner rooms of an MRI suite for a plurality of bifurcated equipment systems. In this particular arrangement, the communication system accommodates three bifurcated systems. First, as described above for the bifurcated injection system, the controller 100c and injection control unit 200c communicate via antenna coupling 400 through their transceivers 330c and 320c, respectively. Second, another bifurcated equipment system 500a,b communicates, via antenna coupling 400, through transceiver 520 in scanner room 150 and transceiver 530 in control room 155. Third, yet another bifurcated system 600a,b communicates, via antenna coupling 400, through transceiver 620 in scanner room 150 and transceiver 630 in control room 155. The second bifurcated system 500a,b may, for example, be a patient monitoring system. The third bifurcated system 600a,b may be an infusion pump whose controller 600a resides in control room 155 and its pump mechanism 600b in scanner room 150.

In this variation of the preferred embodiment, all of the bifurcated equipment systems communicate through the isolation barrier 160 via one antenna coupling 400. It should be apparent, however, that a communication system can be set up using multiple antenna couplings according to the preferred embodiment of the present invention. In such a communication system, each antenna coupling 400 could be allocated to handle transmissions between the separate pieces of only one particular bifurcated system. For this approach, multiple antenna couplings may be useful as a way to deal with the effects of multipath signal transmission, particularly in scanner room 150, which is likely to be a highly reflective environment due not only to the metallic nature of shield 160 but also to the equipment typically found within scanner room 150. Alternatively, such a communication system may have one antenna coupling 400 handling the transmissions for a plurality of bifurcated equipment systems, with another antenna coupling 400 handling the transmissions for just one. According to yet another alternative, such a communication system may have multiple antenna couplings 400 each of which designed to convey transmissions between all of the bifurcated systems. In this case, each separate antenna coupling 400, and particularly their filters, should be designed to avoid significant phase delay and thus avoid destructive interference of the RF signals radiating from the antenna couplings 400.

In a further variation of the preferred embodiment, the antenna coupling of the present invention may be comprised of a plurality of first antennas each of which interconnected to one of a plurality of second antennas. Each antenna pair would preferably be configured in the same manner as described above in connection with single antenna coupling 400. In this multiple antenna pair arrangement, each of the first antennas would preferably be positioned on one side of the isolation barrier with each of the second antennas on the other side. Each antenna pair would also preferably include a filter, akin to filter 403 described above. Each filter would assure that communication through its pair of antennas would occur over the desired range (s) of frequencies outside the range of, and without adversely affecting, the operation of the MRI suite.

Similar to the possibilities for single antenna coupling 400, one such antenna pair could operate, for example, in the 2.4–2.48 GHz band according to the IEEE 802.11b standard. Another antenna pair could operate in the 5 GHz band according to the IEEE 802.11a standard. The 900 MHz ISM band is another possibility. Yet another antenna pair could operate in the 700 MHz or other portion of the Wireless Medical Telemetry Service (WMTS) band allocated to medical telemetry by the FCC. For short-range remote control frequency applications, the 400 MHz band could be used (e.g., remotely turning on and off an injection system or other bifurcated equipment system).

The antenna coupling 400 of the present invention serves as a signal repeater and thus avoids the shortcomings inherent to both the prior art and the previously disclosed embodiments. However, one or more signal repeaters 700, akin to the intermediate communication units 228a discussed in the context of the third embodiment, may be also employed, if necessary, to widen the coverage area should the signal strength prove inadequate in certain parts of the scanner room 150. Such signal repeater(s) 700 would need to be adapted, of course, to the frequency band of the transceivers for the particular bifurcated system(s) with which it/they would be used. In the case where the antenna coupling 400 of FIG. 6A is attached to a door 180, for example, the signal repeater(s) 700 may be placed near the top of the door frame, even on each side of the door, to amplify and rebroadcast the signals conveyed by antenna coupling 400. The use of signal repeaters 700 or other such means would further assure that the separate pieces of each bifurcated system could be moved freely within the scanner and controls rooms 150 and 155, respectively, without losing communication with its counterpart.

The invention also provides a method of communicating across the isolation barrier 160 of an MRI suite. The method includes the steps of: (a) positioning a first transceiver 320c within scanner room 150; (b) positioning a second transceiver 330c within control room 155; (c) interconnecting a first antenna 401 and a second antenna 402; and (d) positioning the first and second antennas 401 and 402 within the MRI suite. The first antenna 401 is positioned within scanner room 150 approximate an interior side of the barrier 160, and is capable of receiving from and transmitting to the first transceiver 320c. The second antenna 402 is positioned within control room 155 approximate an exterior side of barrier 160, and is capable of receiving from and transmitting to the second transceiver 330c. The method also includes the step of configuring the first and second transceivers 320c and 330c to use a desired range(s) of radio frequencies outside the range of operation of the MRI suite in communicating across barrier 160 via the first and second antennas, thus avoiding adverse affects upon the operation of scanner 300 in the MRI suite. In a related aspect, the method may also include the step of connecting one or more filters 403 between the first and second antennas 401 and 402, preferably on the exterior side of shield 160, to prevent radio frequencies outside of the desired range(s) from being transmitted across the isolation barrier 160.

Although the invention has been described in detail in connection with the above embodiments and/or examples, it is to be understood that such detail is solely for that purpose. Variations can be made by those skilled in the art without departing from the invention. The scope of the invention is indicated by the following claims rather than by the foregoing description. All changes and variations which come within the meaning, and range of equivalency, of the claims are to be embraced within their scope.

Accordingly, to promote the progress of science and the useful arts, we secure for ourselves by Letters Patent exclusive rights to all subject matter embraced by the following claims for the time prescribed by the Patent Act.

We claim:

1. A system of communicating for an injection system for use within a magnetic resonance imaging (MRI) suite, said MRI suite having a scanner room, a control room and a barrier separating said scanner and said control rooms, said system comprising:
   (a) a first transceiver situated within said scanner room in an injection control unit of said injection system;
   (b) a second transceiver situated within said control room in a controller of said injection system;
   (c) a first antenna positioned within said scanner room approximate an interior side of said barrier, said first antenna being capable of receiving from and transmitting to said first transceiver; and
   (d) a second antenna positioned within said control room approximate an exterior side of said barrier, said second antenna being capable of receiving from and transmitting to said second transceiver;
   wherein said first and said second antennas are interconnected through said barrier to form an antenna coupling thus enabling said controller and said injection control unit to communicate therethrough across said barrier using a desired range of radio frequencies outside a range of, and without adversely affecting, operation of said MRI suite.

2. The system claimed in claim 1 wherein said antenna coupling further comprises a filter connected between said first and said second antennas to prevent radio frequencies outside of said desired range from being transmitted across said barrier.

3. The system claimed in claim 2 wherein said filter is one of a highpass filter, a bandpass filter, and a bandstop filter at a Larmor frequency of a main magnet in said scanner room.

4. The system claimed in claim 1 wherein said first and said second antennas employ a circularly polarized design.

5. The system claimed in claim 1 wherein said first and said second antennas are directive antennas.

6. The system claimed in claim 1 wherein said first and said second antennas are broadband antennas to allow for communication at several radio frequencies within said desired range.

7. The system claimed in claim 1 wherein said desired range of said radio frequencies is at least approximately double a Larmor frequency of a main magnet in said scanner room.

8. The system claimed in claim 1 further comprising at least one signal repeater positioned within said scanner room for relaying communications between said first antenna and said first transceiver.

9. The system claimed in claim 1 further comprising a plurality of signal repeaters positioned within said scanner room for relaying communications between said first antenna and said first transceiver.

10. The system claimed in claim 1 further comprising an amplifier connected between at least one of (i) said first antenna and said second antenna on said exterior side of said barrier and (ii) said first antenna and said second antenna on said interior side of said barrier.

11. The system claimed in claim 1 wherein at least one of said first and said second transceivers employs a filter to prevent radio frequencies outside of said desired range from being transmitted.

12. An antenna coupling for communicating across a barrier to radio frequencies, said antenna coupling comprising:
  (a) a first antenna adapted to be positioned on a first side of said barrier, said first antenna being capable of receiving from and transmitting to a first transceiver disposed on said first side of said barrier; and
  (b) a second antenna adapted to be positioned on a second side of said barrier, said second antenna being capable of receiving from and transmitting to a second transceiver disposed on said second side of said barrier;
  said first and said second antennas being interconnected through said barrier to form said antenna coupling and thereby enable said first and said second transceivers to communicate therethrough across said barrier over a desired range of said radio frequencies.

13. The antenna coupling claimed in claim 12 further comprising a filter interconnected between said first and said second antennas to prevent radio frequencies outside of said desired range from being transmitted across said barrier.

14. The antenna coupling claimed in claim 13 wherein:
  (a) said filter is a microstrip filter sandwiched insulatively between conductive layers;
  (b) said first antenna is a patch antenna interconnected to one end of said microstrip filter and capable of being positioned on said first side of said barrier; and
  (c) said second antenna is a patch antenna interconnected to the other end of said microstrip filter and capable of being positioned on said second side of said barrier.

15. The antenna coupling claimed in claim 14 wherein one of said conductive layers of said antenna coupling is adapted to be grounded and affixed to at least one of a jamb and an edge of a door of said barrier with said first and said second antennas being situated on said first and said second sides of said barrier, respectively.

16. The antenna coupling claimed in claim 14 wherein said antenna coupling has a bracketshaped configuration with said first and said second patch antennas connected at a predetermined angle at opposite ends of said microstrip filter.

17. The antenna coupling claimed in claim 12 wherein said antenna coupling is adapted to be affixed to an entry way through said barrier with said first and said second antennas being situated on said first and said second sides of said barrier, respectively.

18. The antenna coupling claimed in claim 13 wherein said filter is interconnected between said first and said second antennas so as to be positioned on said second side of said barrier.

19. The antenna coupling claimed in claim 13 wherein said filter is one of a highpass filter, a bandpass filter, and a bandstop filter at a Larmor frequency of a main magnet in an MRI suite.

20. The antenna coupling claimed in claim 12 wherein said first and said second antennas employ a circularly polarized design.

21. The antenna coupling claimed in claim 12 wherein said first and said second antennas are directive antennas.

22. The antenna coupling claimed in claim 12 wherein said first and said second antennas are broadband antennas to allow for communication at several radio frequencies within said desired range.

23. The antenna coupling claimed in claim 12 wherein said desired range of said radio frequencies is at least approximately double a Larmor frequency of a main magnet in an MRI suite.

24. The antenna coupling claimed in claim 12 further comprising an amplifier connected between at least one of (i) said first antenna and said second antenna on said first side of said barrier and (ii) said first antenna and said second antenna on said second side of said barrier.

25. An antenna coupling for communicating across a barrier to radio frequencies, said antenna coupling comprising:
  (a) a first antenna positioned on a first side of said barrier;
  (b) a second antenna positioned on a second side of said barrier, said first and said second antennas interconnected through said barrier to enable a desired range of said radio frequencies to be transmissible through said barrier via said first and said second antennas; and
  (c) a filter connected between said first and said second antennas to prevent radio frequencies outside of said desired range from being transmitted across said barrier.

26. A system of communicating for use within a magnetic resonance imaging (MRI) suite, said MRI suite having a scanner room, a control room and a barrier separating said scanner and said control rooms, said system comprising:
  (a) a first transceiver situated within said scanner room associated with a first piece of equipment;
  (b) a second transceiver situated within said control room associated with a second piece of equipment;
  (c) a first antenna positioned within said scanner room approximate an interior side of said barrier, said first antenna being capable of receiving from and transmitting to said first transceiver; and
  (d) a second antenna positioned within said control room approximate an exterior side of said barrier, said second antenna being capable of receiving from and transmitting to said second transceiver;
  wherein said first and said second antennas are interconnected through said barrier to form an antenna coupling thus enabling said first and said second pieces of equipment to communicate therethrough across said barrier using a desired range of radio frequencies outside a range of, and without adversely affecting, operation of said MRI suite.

27. The system claimed in claim 26 wherein said antenna coupling further comprises a filter connected between said first and said second antennas to prevent radio frequencies outside of said desired range from being transmitted across said barrier.

28. The system claimed in claim 26 wherein said first and said second pieces of equipment are an injection control unit and a controller therefor, respectively, of an injection system.

29. The system claimed in claim 26 wherein at least one of said first and said second transceivers employs a filter to prevent radio frequencies outside of said desired range from being transmitted.

30. A method of communicating across an isolation barrier separating a scanner room and a control room of a magnetic resonance imaging (MRI) suite, said method comprising the steps of:
(a) positioning a first transceiver within said scanner room;
(b) positioning a second transceiver within said control room;
(c) interconnecting a first antenna and a second antenna;
(d) positioning said first and said second antennas within said MRI suite such that (i) said first antenna is positioned within said scanner room approximate an interior side of said isolation barrier and is capable of receiving from and transmitting to said first transceiver and (ii) said second antenna is positioned within said control room approximate an exterior side of said isolation barrier and is capable of receiving from and transmitting to said second transceiver; and
(e) configuring said first and said second transceivers to use a desired range of radio frequencies outside a range of operation of said MRI suite in communicating across said isolation barrier via said first and said second antennas, and thus avoiding adverse affects upon an operation of a scanner in said MRI suite.

31. The method claimed in claim 30 further comprising the step of connecting a filter between said first and said second antennas to prevent radio frequencies outside of said desired range from being transmitted across said isolation barrier.

32. The method claimed in claim 30 wherein said first and said second transceivers are associated with and allow communication between an injection control unit and a controller therefor, respectively, of an injection system.

33. A system for communicating across an isolation barrier separating a scanner room and a control room of a magnetic resonance imaging (MRI) suite, said MRI suite for accommodating a plurality of bifurcated equipment systems, each of said bifurcated equipment systems having an interior portion for placement within said scanner room and an exterior portion for placement within said control room, said system comprising:
(a) a first antenna positioned within said scanner room, said first antenna being capable of receiving from and transmitting to a plurality of interior transceivers situated within said scanner room, each of said interior transceivers being associated with said interior portion of one of said bifurcated equipment systems corresponding thereto; and
(b) a second antenna positioned within said control room and interconnected to said first antenna through said isolation barrier to form an antenna coupling therewith; said second antenna being capable of receiving from and transmitting to a plurality of exterior transceivers situated within said control room, each of said exterior transceivers being associated with said exterior portion of one of said bifurcated equipment systems corresponding thereto;
each of said exterior transceivers and said interior transceiver corresponding thereto forming a transceiver pair for one of said bifurcated equipment systems through which said interior and said exterior portions thereof communicate through said antenna coupling across said isolation barrier using a desired range of radio frequencies assigned thereto outside a range of, and without adversely affecting, operation of said MRI suite.

34. The system claimed in claim 33 wherein said antenna coupling further comprises a filter connected between said first and said second antennas to prevent radio frequencies outside of all of said desired ranges of said transceiver pairs from being transmitted across said isolation barrier.

35. The system claimed in claim 34 wherein said filter is one of a highpass filter, a bandpass filter, and a bandstop filter at a Larmor frequency of a main magnet in said scanner room.

36. The system claimed in claim 33 wherein said first and said second antennas employ a circularly polarized design.

37. The system claimed in claim 33 wherein said first and said second antennas are directive antennas.

38. The system claimed in claim 33 wherein said desired ranges of said radio frequencies of said transceiver pairs are at least approximately double a Larmor frequency of a main magnet in said scanner room.

39. The system claimed in claim 33 wherein:
(a) said filter is a microstrip filter sandwiched insulatively between conductive layers;
(b) said first antenna is a patch antenna interconnected to one end of said microstrip filter and capable of being positioned on an interior side of said isolation barrier; and
(c) said second antenna is a patch antenna interconnected to the other end of said microstrip filter and capable of being positioned on an exterior side of said isolation barrier.

40. The system claimed in claim 39 wherein one of said conductive layers of said antenna coupling is adapted to be grounded and affixed to at least one of a jamb and an edge of a door of said barrier with said first and said second antennas being situated on said first and said second sides of said barrier, respectively.

41. The system claimed in claim 39 wherein said antenna coupling has a bracketshaped configuration with said first and said second patch antennas connected at a predetermined angle at opposite ends of said microstrip filter.

42. The system claimed in claim 33 further comprising at least one signal repeater positioned within said scanner room for relaying communications between said first antenna and said first transceiver.

43. The system claimed in claim 33 further comprising a plurality of signal repeaters positioned within said scanner room for relaying communications between said first antenna and said first transceiver.

44. The system claimed in claim 33 further comprising an amplifier connected between at least one of (i) said first and said second antennas and positioned within said scanner room and (ii) said first and said second antennas and positioned within said control room.

45. The system claimed in claim 33 wherein at least one of said interior and said exterior transceivers employs a filter to prevent radio frequencies outside of said desired range(s) from being transmitted.

46. An antenna coupling for communicating across a barrier to radio frequencies, said antenna coupling comprising:
(a) a plurality of interior antennas each of which adapted to be positioned on an interior side of said barrier, each of said interior antennas being capable of receiving from and transmitting to at least one interior transceiver disposed on said interior side of said barrier; and
(b) a plurality of exterior antennas each of which adapted to be positioned on an exterior side of said barrier, each of said exterior antennas being capable of receiving from and transmitting to at least one exterior transceiver disposed on said exterior side of said barrier, each of said interior transceivers and said exterior transceiver corresponding thereto forming a transceiver pair;

each of said interior antennas and said exterior antenna corresponding thereto being interconnected through said barrier to form an antenna pair for enabling said transceiver pair(s) corresponding thereto to communicate therethrough across said barrier over a desired range of said radio frequencies.

47. The antenna coupling claimed in claim 46 further comprising a filter interconnected between said first and said second antennas of each of said antenna pairs to prevent radio frequencies outside of said desired range from being transmitted across said barrier.

48. The antenna coupling claimed in claim 46 further comprising a filter interconnected within at least one of said antenna pairs to prevent radio frequencies outside of said desired range from being transmitted across said barrier.

* * * * *

UNITED STATES PATENT AND TRADEMARK OFFICE
CERTIFICATE OF CORRECTION

| | | |
|---|---|---|
| PATENT NO. | : 7,221,159 B2 | Page 1 of 1 |
| APPLICATION NO. | : 10/064846 | |
| DATED | : May 22, 2007 | |
| INVENTOR(S) | : Griffiths et al. | |

It is certified that error appears in the above-identified patent and that said Letters Patent is hereby corrected as shown below:

Title Page

Item (63) Delete section "RELATED U.S. APPLICATION DATA"

Column 1

Lines 5 through 13, delete "CROSS REFERENCE TO RELATED APPLICATIONS…" through "…by reference."

Column 19

Line 48, change "bracketshaped" to --bracket-shaped--

Column 22

Line 36, change "bracketshaped" to --bracket-shaped--
Line 59, after "which" add --is--
Line 64, after "which" add --is--

Column 23

Line 3, change "transceiver" to --transceivers--
Line 5, change "antenna" to --antennas--

Signed and Sealed this

Eleventh Day of September, 2007

JON W. DUDAS
*Director of the United States Patent and Trademark Office*